United States Patent
Hergenrother et al.

(10) Patent No.: US 9,682,060 B2
(45) Date of Patent: Jun. 20, 2017

(54) SMALL MOLECULES THAT INDUCE INTRINSIC PATHWAY APOPTOSIS

(71) Applicant: The Board of Trustees of the University of Illinois, Urbana, IL (US)

(72) Inventors: Paul J. Hergenrother, Champaign, IL (US); Karson S. Putt, Champaign, IL (US); Rahul Palchaudhuri, Cambridge, MA (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 0 days.

(21) Appl. No.: 15/295,921

(22) Filed: Oct. 17, 2016

(65) Prior Publication Data
US 2017/0105963 A1   Apr. 20, 2017

Related U.S. Application Data

(60) Provisional application No. 62/242,347, filed on Oct. 16, 2015.

(51) Int. Cl.
*A61K 31/343* (2006.01)
*A61K 31/11* (2006.01)

(52) U.S. Cl.
CPC ............ *A61K 31/343* (2013.01); *A61K 31/11* (2013.01)

(58) Field of Classification Search
CPC .............................. A61K 31/343; A61K 31/11
USPC ........................................................ 514/462
See application file for complete search history.

(56) References Cited

U.S. PATENT DOCUMENTS 7,157,491 B2   1/2007   Mewshaw et al.

OTHER PUBLICATIONS

Curtin et al., Nitrosation Reactions of Primary Vinylamines. Possible Divalent Carbon Intermediates, Feb. 20, 1965, Journal of the American Chemical Society, 87:4, 863-873.*

Bosserman, L., et al., "The Microculture-Kinetic (MICK) Assay: The Role of a Drug-Induced Apoptosis Assay in Drug Development and Clinical Care," Cancer Res.; 72(16):3901-3905; Aug. 15, 2012.
Botham, R.C., et al., "Dual Small-Molecule Targeting of Procaspase-3 Dramatically Enhances Zymogen Activation and Anticancer Acitivyt," J Am Chem Soc.;136(4):1312-1319; Jan. 29, 2014.
Boyé, O., et al., "Deaminocolchinyl Methyl Ether. Synthesis from 2,3,4,4'-Tetramethoxybiphenyl-2-carbaldehyde. Comparison of Antitubulin Effects of Deaminocolchiryl Methyl Ether and Dehydro Analogs," Helvetica Chimca Acta; 72(8):1690-1696; Dec. 13, 1989.
Curtin, D.Y., et al., "Nitrosation Reactions of Primary Vinylamines. 3-Amino-2-phenylindenone1." J. Am. Chem. Soc.; 87(4):874-882; Feb. 1965.
Palchaudhuri, R., et al., "A Small Molecule that Induces Intrinsic Pathway Apoptosis with Unparalleled Speed," Cell Rep.; 13(9):2027-2036; Dec. 1, 2015.
Wolpaw, A.J., et al., "Modulator Profiling Identifies Mechanisms of Small Molecule-Induced Cell Death," Proc Natl Acad Sci U S A.; 108(39):E771-E780, Sep. 27, 2011.

* cited by examiner

*Primary Examiner* — Kristin Vajda
(74) *Attorney, Agent, or Firm* — Haukaas Fortius PLLC; Michael H. Haukaas

(57) ABSTRACT

Apoptosis is generally believed to be a process that requires several hours, in contrast to non-programmed forms of cell death that can occur in minutes. Our findings challenge the time-consuming nature of apoptosis. We describe herein the discovery and characterization of a small molecule, named Raptinal, which initiates intrinsic pathway caspase-dependent apoptosis within minutes, in multiple different cell lines. Comparison to a mechanistically diverse panel of apoptotic stimuli reveals Raptinal-induced apoptosis proceeds with unparalleled speed. The rapid phenotype enabled identification of the critical roles of mitochondrial voltage-dependent anion channel function, mitochondrial membrane potential/coupled respiration, and mitochondrial complex I, III and IV function for apoptosis induction. Use of Raptinal in whole organisms demonstrates its utility to study apoptosis in vivo for a variety of applications. Overall, rapid inducers of apoptosis are powerful tools that will be used in a variety of settings to generate further insight into the apoptotic machinery.

20 Claims, 19 Drawing Sheets

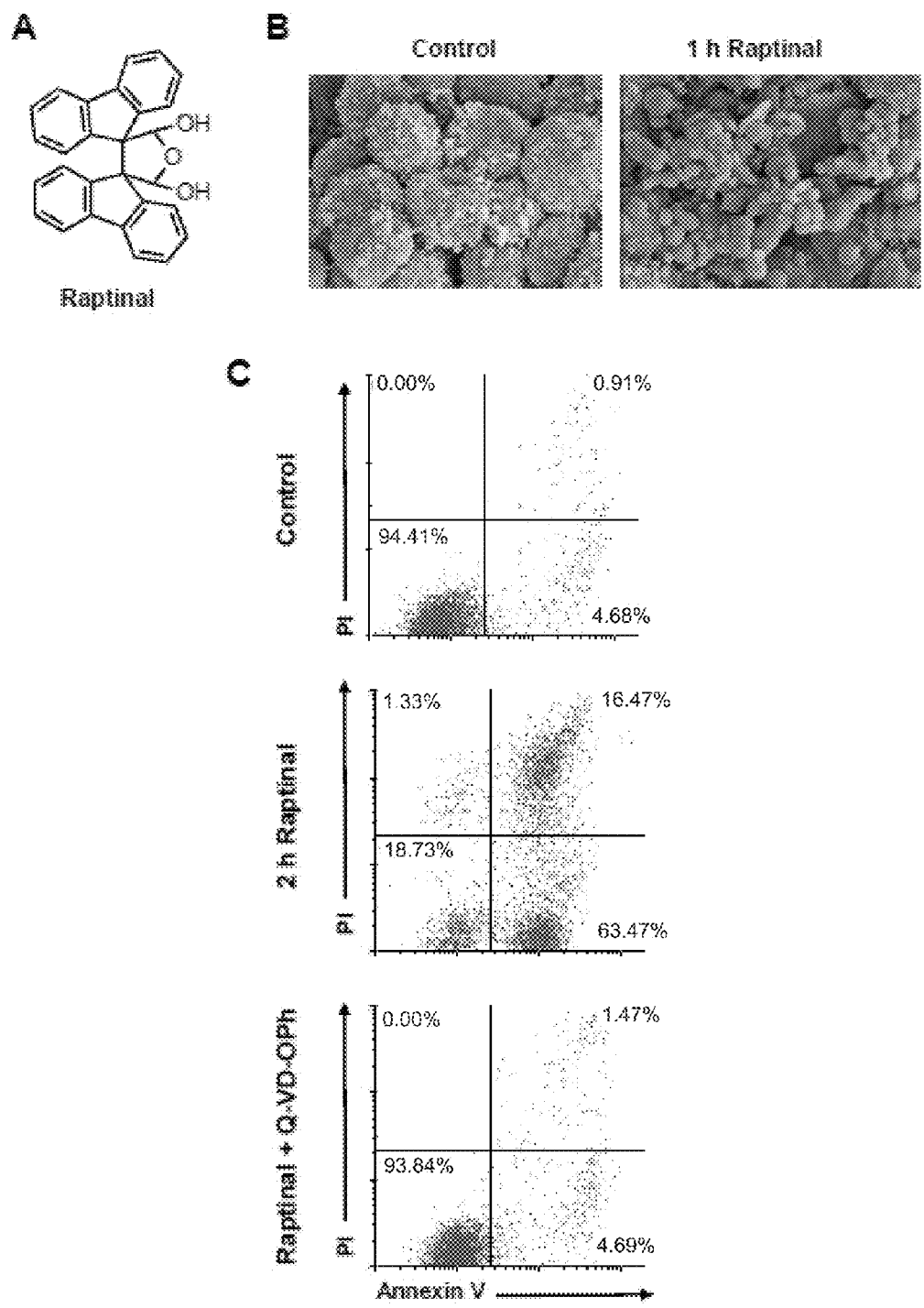
Fig. 1A-C

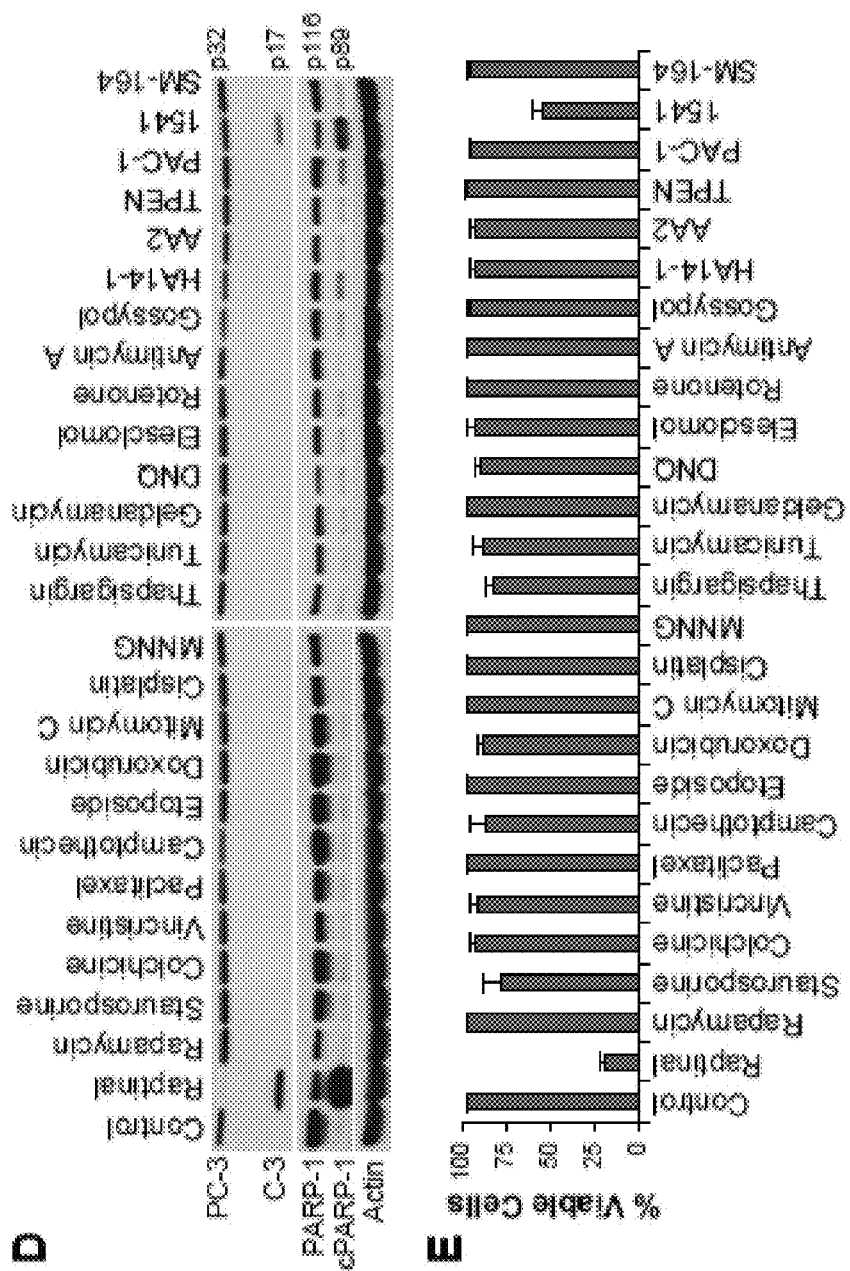
Fig. 1D-E

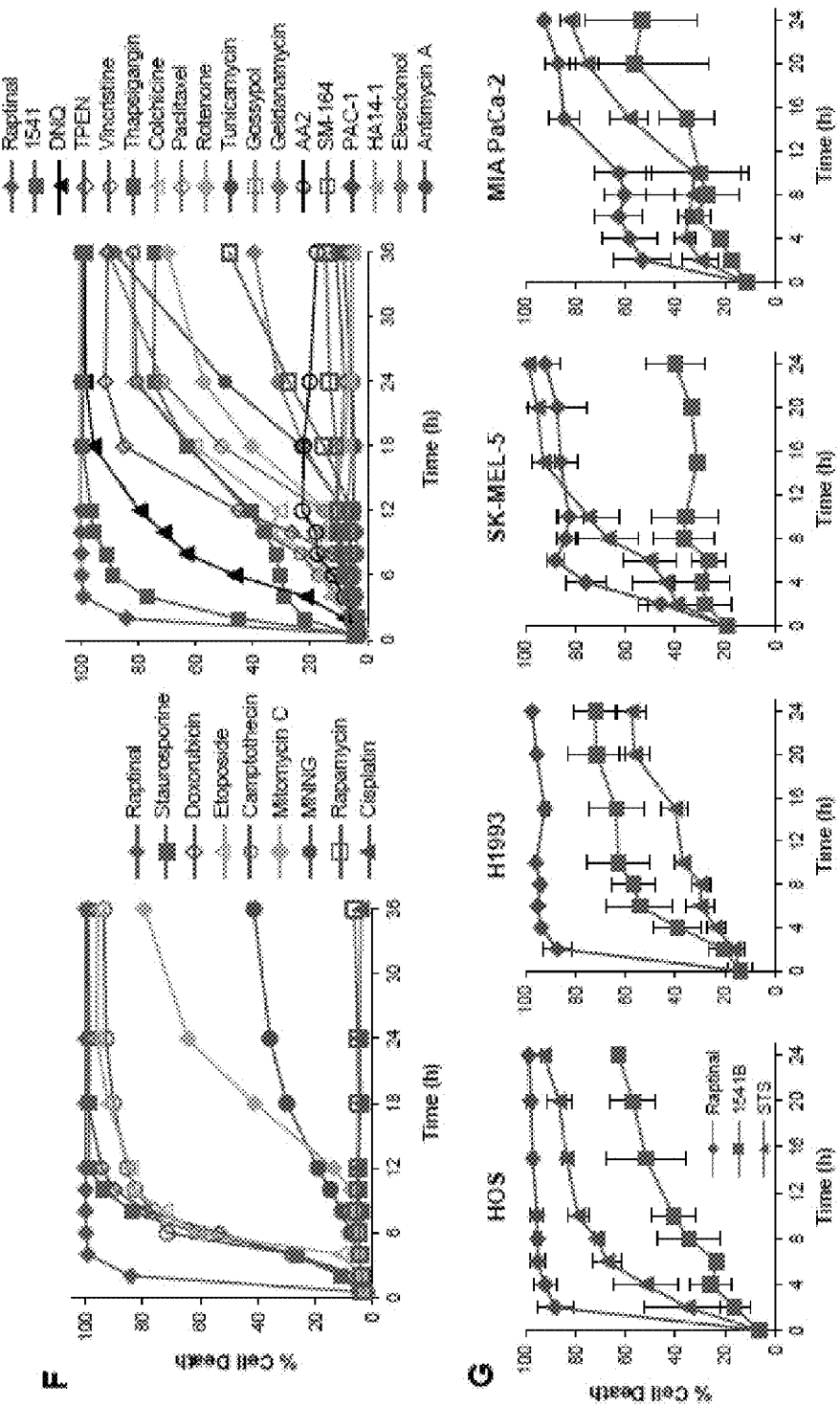
Fig. 1F-G

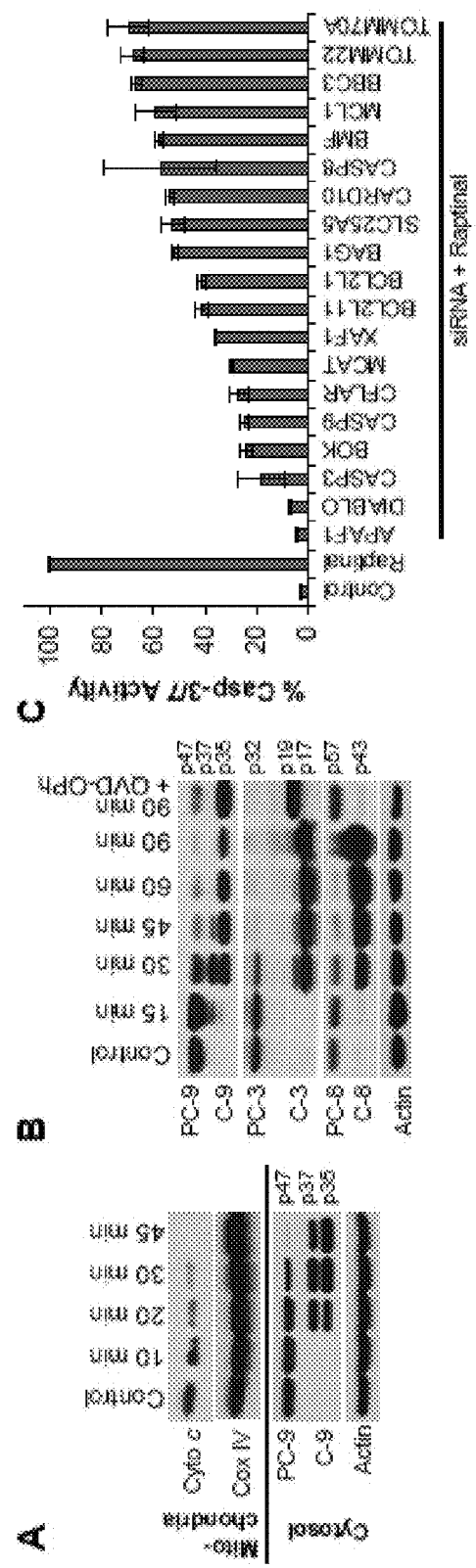
Fig. 2A-C

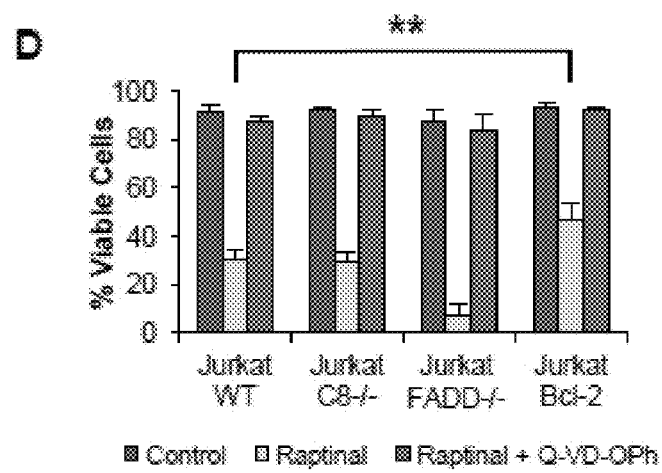
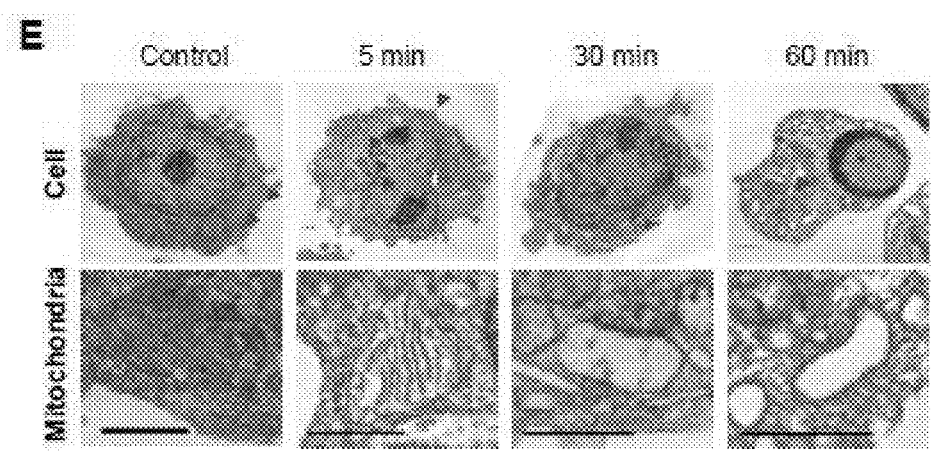
Fig. 2D-E

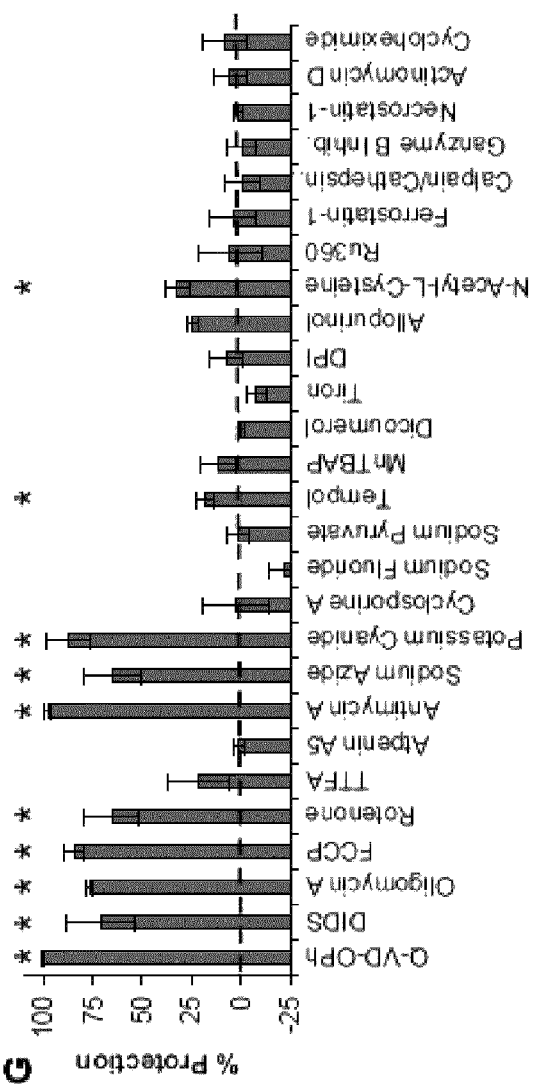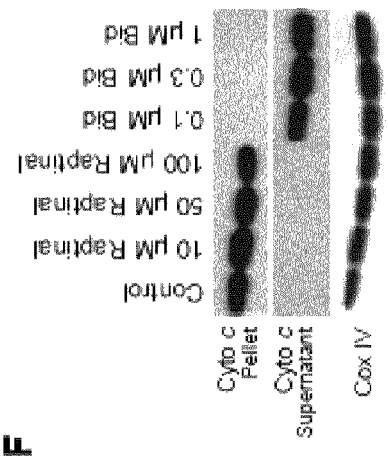
Fig. 2F-G

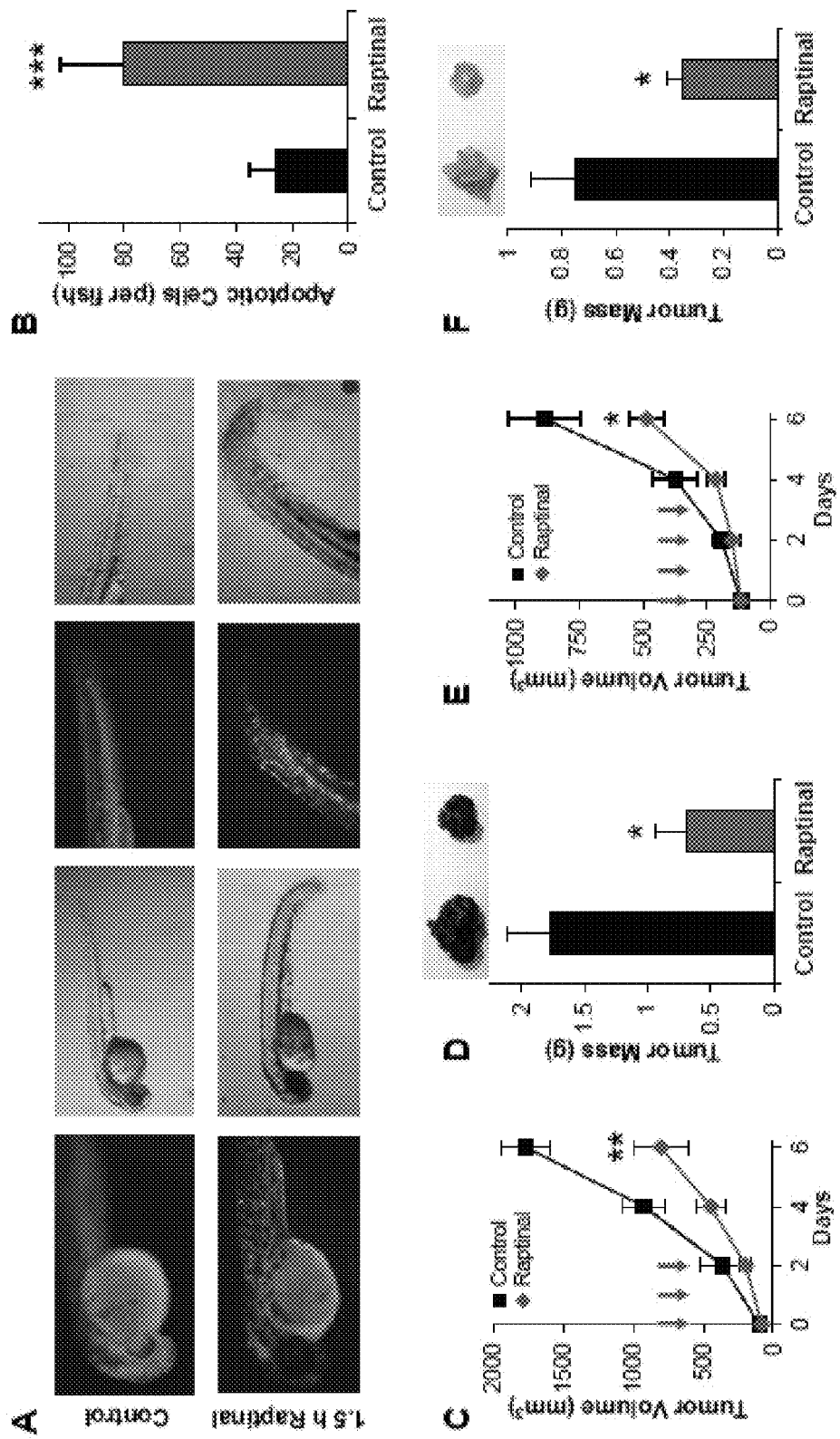
Fig. 3A-F

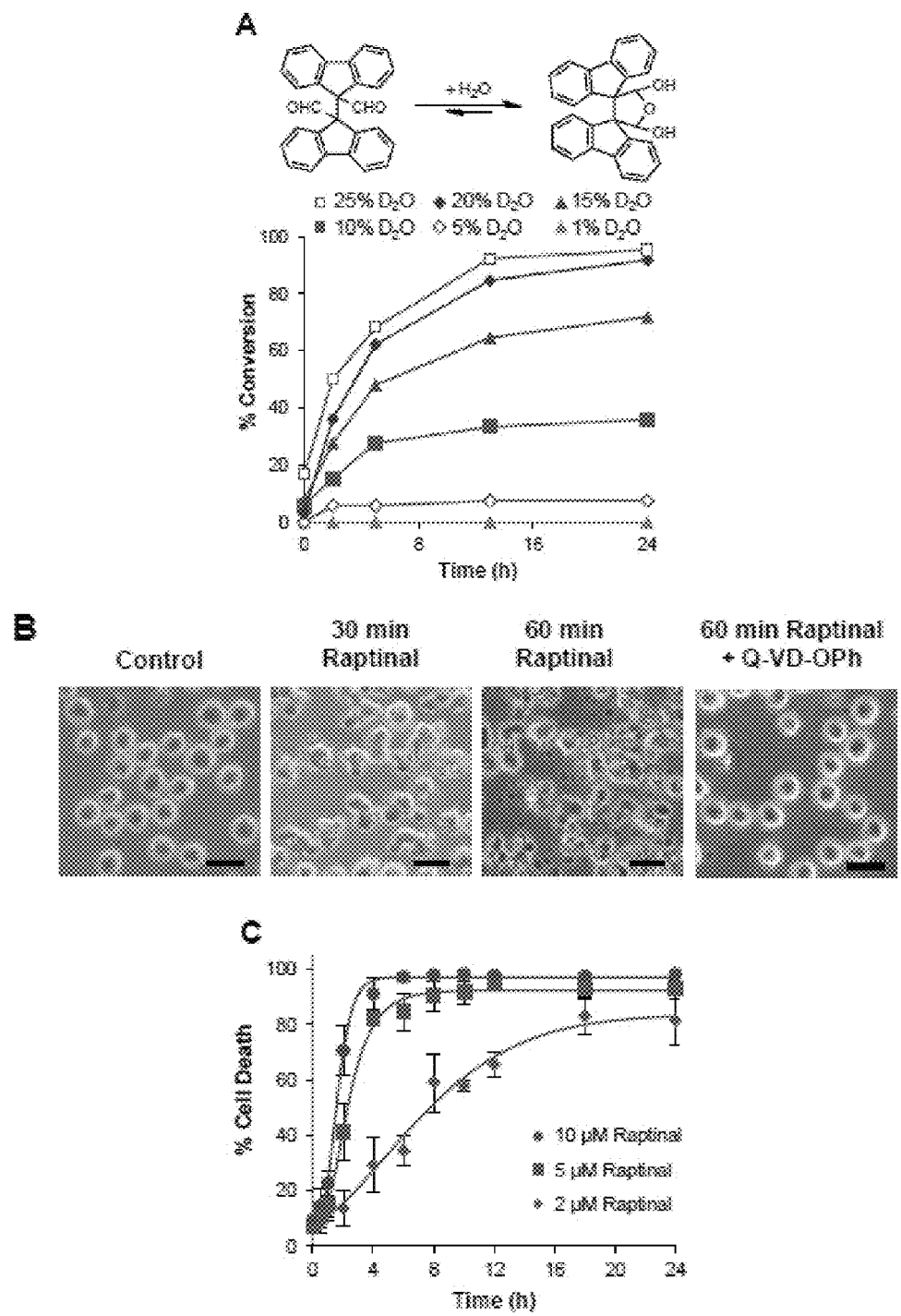
Fig. 4A-C

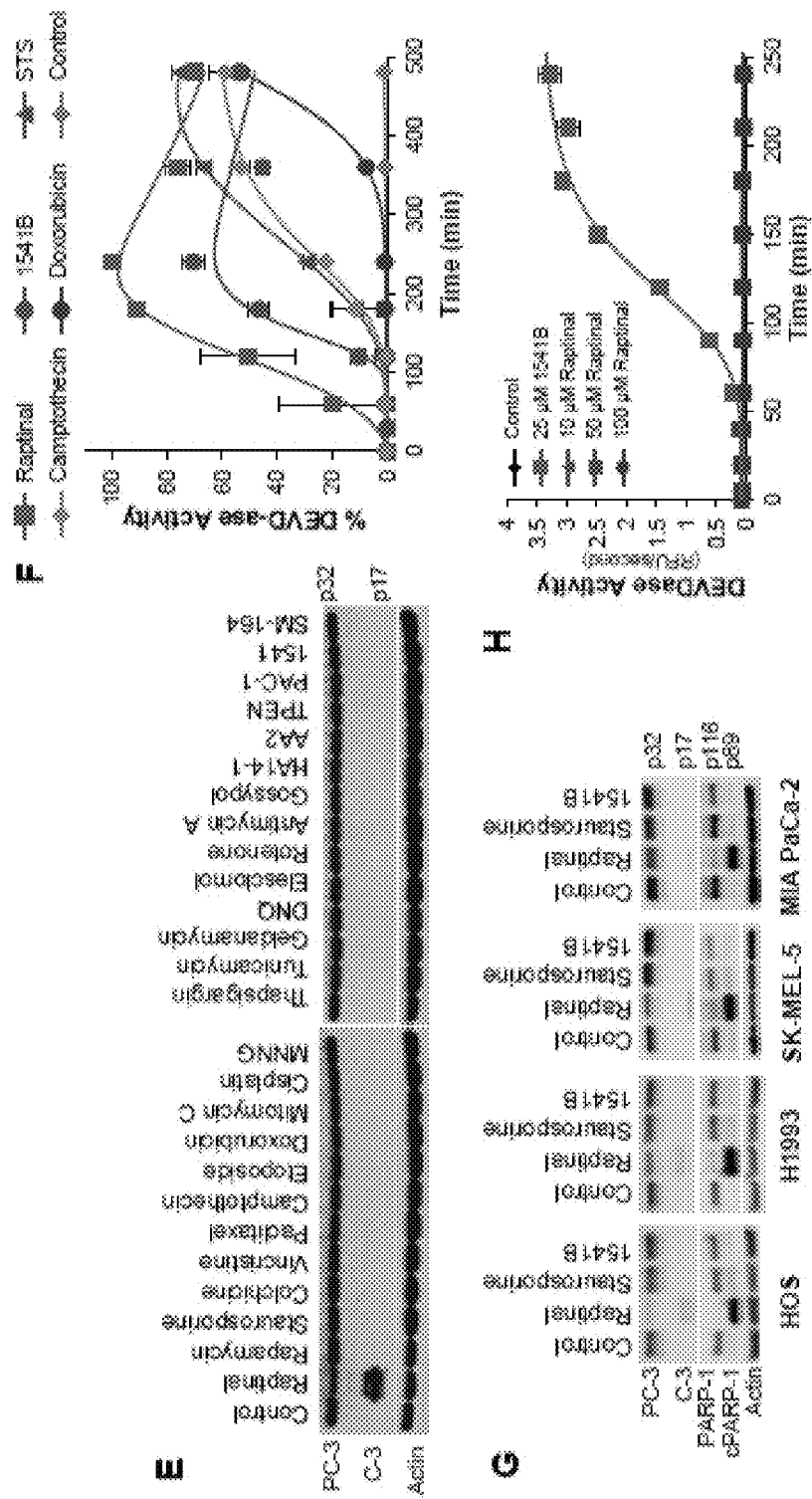
*Fig. 4E-H*

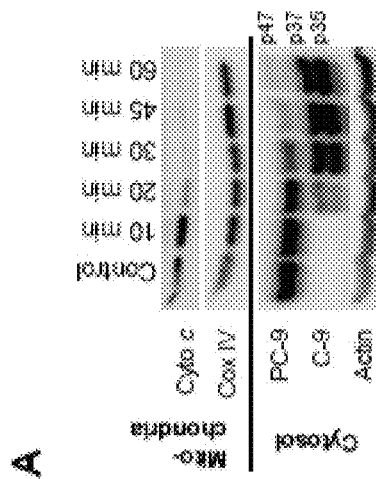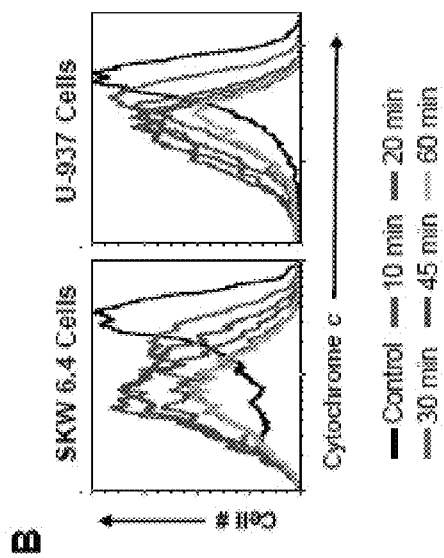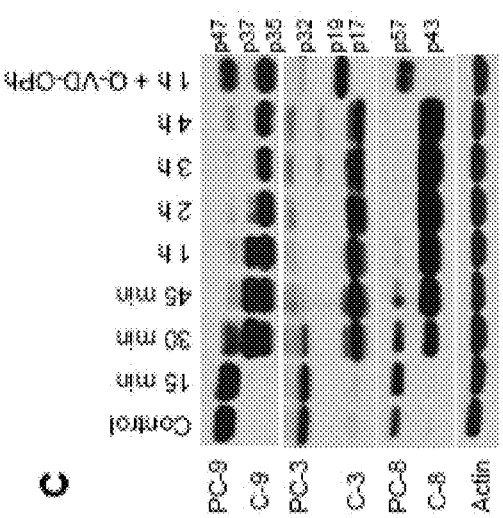
Fig. 5A-C

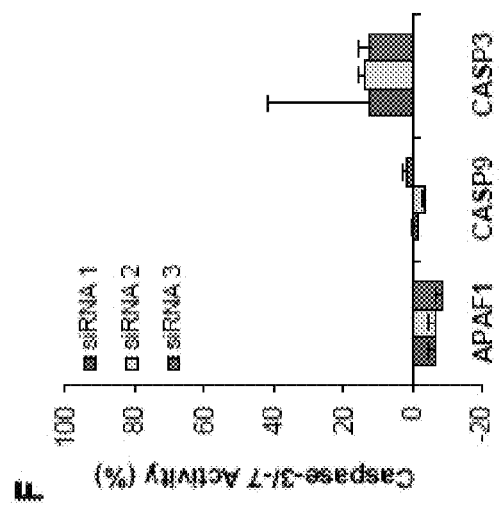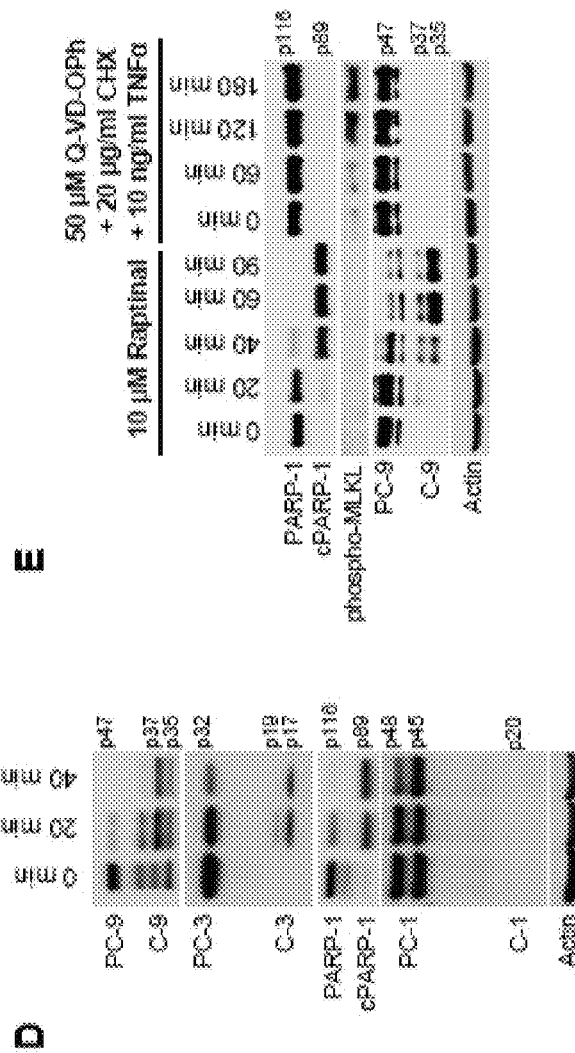
Fig. 5D-F

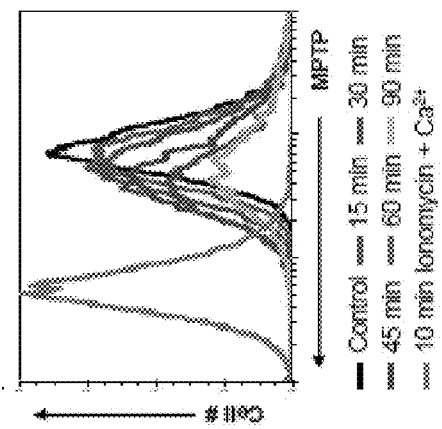
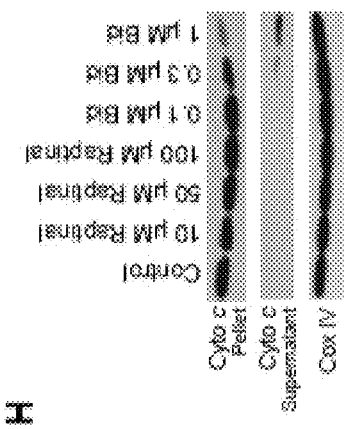
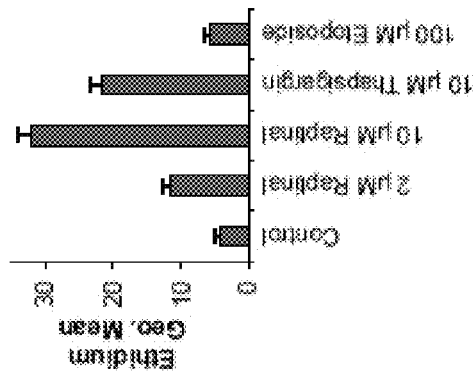
*Fig. 5G-I*

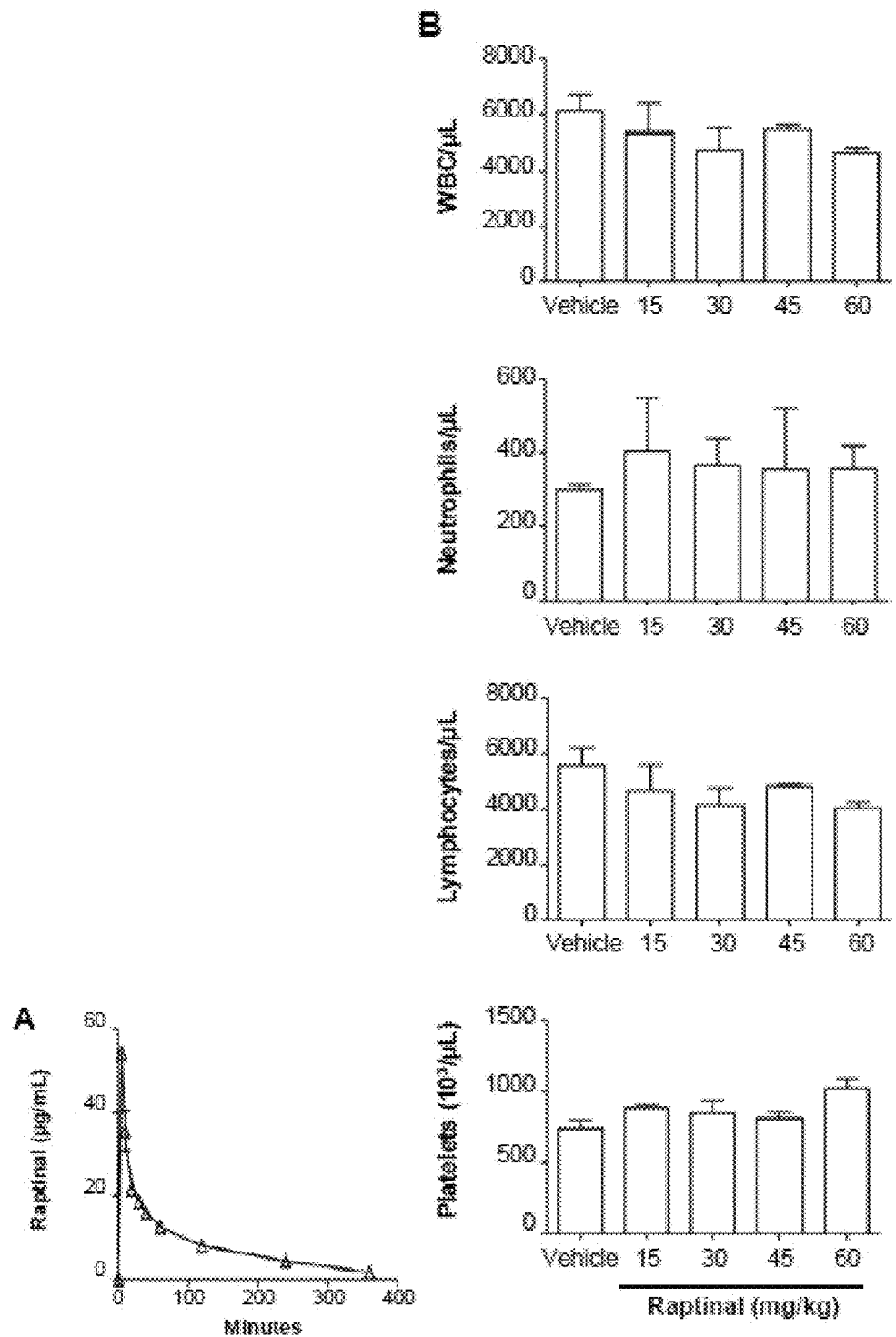
Fig. 6A-B

| Compound | 24 h IC$_{50}$ (µM) | 24 h IC$_{50}$ Curve |
|---|---|---|
| S8 (structure: fluorene with F$_3$COC and COCF$_3$ groups) | > 100 | |
| S9 (structure: fluorene with MeO$_2$C and CO$_2$Me groups) | > 100 | |
| S10 (structure: Br-substituted fluorene with OHC and CHO groups) | 6.5 ± 1.6<br><br>% Cell Death at 2 h (10 µM treatment): 6.3 ± 0.8 | |
| S11 (structure: Cl-substituted fluorene with OHC and CHO groups) | 4.6 ± 0.9<br><br>% Cell Death at 2 h (10 µM treatment): 7.6 ± 1.9 | |

*Fig. 7 (cont.)*

SMALL MOLECULES THAT INDUCE INTRINSIC PATHWAY APOPTOSIS

RELATED APPLICATIONS

This application claims priority under 35 U.S.C. §119(e) to U.S. Provisional Patent Application No. 62/242,347 filed Oct. 16, 2015, which is incorporated herein by reference.

GOVERNMENT SUPPORT

This invention was made with government support under Grant No. R01-CA120439 awarded by the National Institutes of Health. The government has certain rights in the invention.

BACKGROUND

Apoptosis-inducing small molecules typically engage the intrinsic pathway, in which release of mitochondrial cytochrome c induces activation of caspase-9, followed by activation of caspase-3. The rate of apoptosis is dependent on the type and strength of the apoptotic stimuli and the cell type, and a minimum of several hours of activating stimulus is typically required for apoptosis induction through the intrinsic pathway (Goldstein et al., 2000). This lengthy induction period is likely due to rate limiting steps upstream of cytochrome c release such as transcription/translation (Dudgeon et al., 2009; Fridman and Lowe, 2003) or cell cycle dependent responses (Hamada et al., 2009). While the time to cytochrome c release varies, once initiated, cytochrome c release may be complete within 5-10 minutes (Goldstein et al., 2005; Luetjens et al., 2001) regardless of cell type. The kinetics of caspase activation following cytochrome c release may be dependent on the cell type, although in certain cells caspase activation is complete within 20 minutes after initiation (Luo et al., 2001; Rehm et al., 2002).

Agents capable of inducing intrinsic pathway-mediated apoptosis are widely employed in a range of biochemical experiments. Typically, the broad-spectrum kinase inhibitor staurosporine has been the small molecule of choice, as it requires a short time period for induction of apoptosis relative to other agents. Among numerous other experiments, staurosporine has been employed in studies that have identified fundamental regulators of the apoptotic pathway (including Bcl-2 (Yang et al., 1997), CAD/ICAD (Sakahira et al., 1998), AIF (Susin et al., 1999), and multiple others), in proteomics experiments examining the scope of cellular caspase protein substrates (Agard et al., 2012; Dix et al., 2008; Dix et al., 2012; Shimbo et al., 2012), and to help elucidate mechanisms of apoptotic death as induced by small molecules (Wolpaw et al., 2011). However, even staurosporine requires multiple hours for full cytochrome c release from the mitochondria (Bossy-Wetzel et al., 1998; Botham et al., 2014), with apoptotic cell death ensuing. In addition, the pan-kinase inhibition and ever-emerging biological effects elicited by staurosporine (Savitski et al., 2014) complicate interpretation of downstream readouts, as demonstrated by the fact that other proapoptotic agents (e.g. doxorubicin and bortezomib) induce a different pattern of caspase cleavage from staurosporine (Shimbo et al., 2012). A compound that rapidly induces mitochondrial cytochrome c release and apoptosis without prolonged engagement of upstream processes would be especially valuable in these and other cell biology experiments.

The overarching impact of apoptosis in diseases, such as cancer (Fulda, 2007), heart disease (Narula et al., 2006), and neurodegeneration (Ferrer, 2006), highlights the necessity of having resources to study and find regulators involved in programmed cell death.

SUMMARY

Apoptosis is generally believed to be a process that requires several hours, in contrast to non-programmed forms of cell death that can occur in minutes. Our findings challenge the time-consuming nature of apoptosis as we describe the discovery and characterization of a small molecule, named Raptinal, which initiates intrinsic pathway caspase-dependent apoptosis within minutes in multiple cell lines. Comparison to a mechanistically diverse panel of apoptotic stimuli reveals Raptinal-induced apoptosis proceeds with unparalleled speed. The rapid phenotype enabled identification of the critical roles of mitochondrial voltage-dependent anion channel function, mitochondrial membrane potential/coupled respiration, and mitochondrial complex I, III and IV function for apoptosis induction. Use of Raptinal in whole organisms demonstrates its utility to study apoptosis in vivo for a variety of applications. Overall, rapid inducers of apoptosis are powerful tools that will be used in a variety of settings to generate further insight into the apoptotic machinery.

Given the importance of apoptosis, small molecules with unusual mechanistic properties will facilitate discovery of additional apoptotic regulators. Accordingly, we report the identification of a small molecule activator of apoptosis that induces initiation of cytochrome c release from the mitochondria within minutes, and displays potency across multiple cell types and animal models.

Raptinal ([9,9']bifluorenyl-9,9'-dicarbaldehyde) was screened and found to be an anti-cancer agent. In our initial screens against cancer cell lines, we were struck by the potency of Raptinal in inducing death in a variety of cancer cell lines (HL-60, SK-MEL-5, U-937); Raptinal has $IC_{50}$ values in the 150-700 nM range (24 hour assays). Raptinal kills cancer cells at a low concentration (e.g., 1-10 µM) and in a very rapid manner. Further experimentation revealed a very novel property of Raptinal: treatment of cancer cells for very short periods of time (1 hour), followed by extensive washing to remove the compound still resulted in significant cell death at the 24-hour mark. This is a very unusual property for an anticancer compound, as most standard cytotoxic agents we have evaluated (e.g., cisplatin, paclitaxel, and geldanamycin) do not have a similar effect. Accordingly, Raptinal can be used as a therapeutic anticancer agent, optionally in combination with another anticancer agent, or it can be used as a research tool, for example, for elucidating the mechanism of action of other potential drugs or research tools.

Accordingly, the invention provides a compound of Formula I:

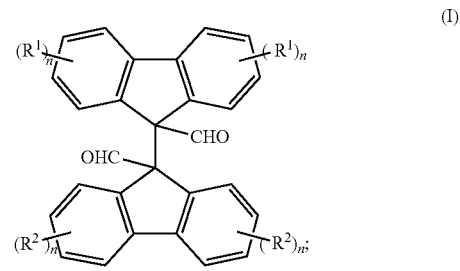

wherein each $R^1$ and $R^2$ is independently H, halo, nitro, $(C_1$-$C_6)$alkyl, $(C_1$-$C_6)$alkoxy, trifluoromethyl, trifluoromethoxy, —CN, $(C_1$-$C_6)$cycloalkyl, or —$N(R^a)_2$ wherein each R is H or $(C_1$-$C_6)$alkyl; and each n is independently 1, 2, 3, or 4; or a salt or solvate thereof. In various embodiments, invention provides a compound of Formula II:

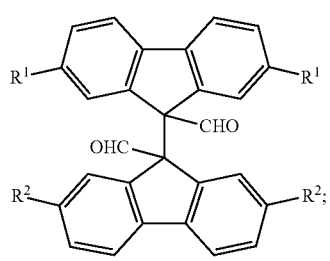

(II)

wherein each $R^1$ and $R^2$ is independently H, halo, nitro, $(C_1$-$C_6)$alkyl, $(C_1$-$C_6)$alkoxy, trifluoromethyl, trifluoromethoxy, —CN, $(C_1$-$C_6)$cycloalkyl, or —$N(R^a)_2$ wherein each R is H or $(C_1$-$C_6)$alkyl, or a salt or solvate thereof. Compounds of Formulas I and II can also be used as their hydrates, e.g., an optionally substituted version of hydrate compound 2 as shown in FIG. 4A. In certain specific embodiments, the compound of Formula I or II is compound 1 or 2:

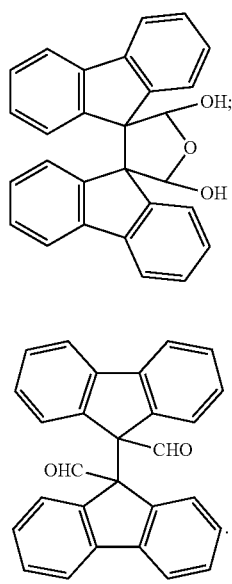

(1)

(2)

The invention also provides a method to induce caspase-dependent apoptosis in an animal cell comprising contacting an animal cell with an effective apoptosis-inducing amount of a compound of Formula I or II, for example, compound 1 or 2:

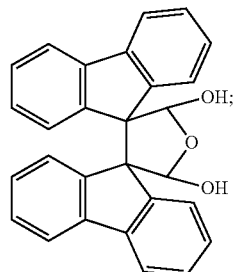

(1)

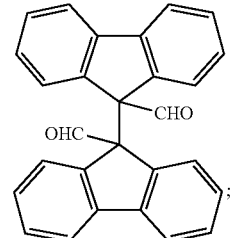

(2)

thereby initiating intrinsic pathway caspase-dependent apoptosis. The animal cell can be a cell in a live animal, or the animal cell can be separate from a mature organism, for example, in an in vitro cell culture. Compound 1 or 2 can be in a solution or formulation in a concentration of about 0.1 μM to about 20 μM. In certain embodiments, compound 1 or 2 is in a solution or formulation in a concentration of about 1 μM, about 2 μM, about 5 μM, about 10 μM, or about 20 μM. In some embodiments, the apoptosis occurs within about 6 hours of contacting the cell. In certain embodiments, the apoptosis occurs within about 180 minutes, or within about 120 minutes, of contacting the cell.

The invention further provides a method of inducing initiation of cytochrome c release from the mitochondria of an animal cell comprising contacting an animal cell with an effective cytochrome c releasing amount of a compound of Formula I or II, for example, compound 1 or compound 2:

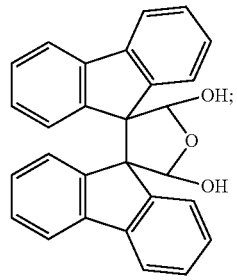

(1)

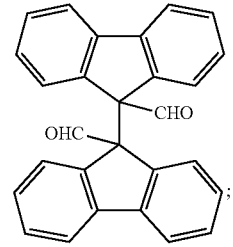

(2)

thereby initiating release of cytochrome c from the animal cell. Release of cytochrome c from the animal cell can be initiated within about 60 minutes of contacting the cell. In some embodiments, release of cytochrome c from the animal cell is initiated within about 30 minutes of contacting the cell. The method can include pretreating the cell with a cytoprotective agent or an inhibitor of a cellular pathway, and assessing cytochrome c release from the cell. In one embodiment, the cytoprotective agent or inhibitor is a mitochondrial inhibitor, an inhibitor of respiration or the electron transport chain, a component of the mitochondrial transition pore, or an inhibitor of glycolysis, reactive oxygen species, calcium dependent pathways, granzyme B, transcription, or translation. The pretreatment can be carried out for an effective amount of time, for example, about 1-3 hours.

In some embodiments, the method includes contacting the cells with a compound of Formula I or II, for example, the compound 1 or 2, in combination with the pan-caspase inhibitor Q-VD-OPh. The method can further include analyzing components of the cell for additional apoptotic regulators, or analyzing enzymatic pathways of the cell to determine effects of the apoptosis. In one embodiment, the cell is contacted with compound 1 or compound 2 in combination with a caspase inhibitor, and the consequences of rapid caspase-9 activation without activation of caspase-8 following caspase-3 activation are evaluated.

The invention additionally provides a method of killing or inhibiting the growth of a cancer cell comprising contacting a cancer cell with an effective anticancer amount of a compound of Formula I or II, for example, compound 1 or 2:

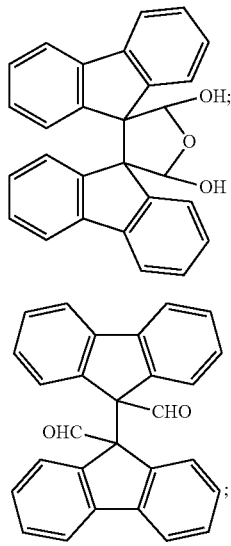

thereby killing or inhibiting the growth of the cancer cell. The cancer cell can be, for example, a breast cancer cell, a cervical cancer cell, a leukemia cell, a lymphoma cell, a lung cancer cell, a melanoma cell, or an osteosarcoma cell.

The invention also provides a method of inducing caspase-3/-7 activity and inducing subsequent PARP-1 cleavage in a cell within 2 hours comprising contacting an animal cell with an effective amount of a compound of Formula I or II, for example, compound 1 or compound 2:

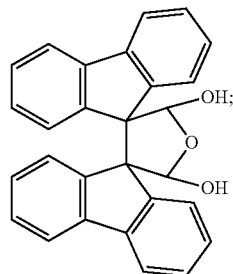

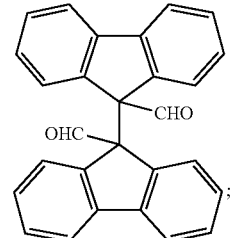

thereby inducing caspase-3/-7 activity and inducing subsequent PARP-1 cleavage in the cell.

The invention yet further provides a composition comprising a compound of Formula I or II in its hydrate (bis-hemi-acetal) form, for example, compound 1:

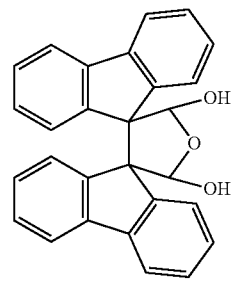

and water. The composition can be used in combination with optional salts and buffers for the methods and analyses described herein.

Without wishing to be bound by any particular theory, there can be discussion herein of beliefs or understandings of underlying principles or mechanisms relating to embodiments of the disclosure. It is recognized that regardless of the ultimate correctness of any explanation or hypothesis, an embodiment of the disclosure can nonetheless be operative and useful. The foregoing and other objects and features of the disclosure will become more apparent from the following detailed description, which proceeds with reference to the accompanying figures. Further embodiments, forms, features, aspects, benefits, objects, and advantages of the present application shall become apparent from the detailed description and figures provided herewith.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention.

FIG. 1A-G. Raptinal rapidly induces apoptosis. A) Structure of Raptinal. B) Scanning electron micrographs of U-937 cells show pronounced apoptotic blebbing after 1 hour of treatment with 10 μM Raptinal (right) versus vehicle control treated cells (left). C) AV/PI graphs of U-937 cells treated with 10 μM Raptinal for 2 hours show transition of cells through the early apoptotic AV+/PI− quadrant that is prevented by the pan-caspase inhibitor Q-VD-OPh. D) Immunoblots of U-937 cells treated with various toxins for 1 hour show more prominent activation of procaspase-3 (PC-3) to caspase-3 (C-3) and cleavage of PARP-1 (cPARP-1) by Raptinal (10 μM) versus 25 other toxins (all tested at 10 μM). E) Cell viability of U-937 cells assessed by AV/PI after 2 hour treatment with 10 μM Raptinal and 25 other small molecules (all tested at 10 μM). Data represent the mean±SD from 3 independent experiments. F) Time course analysis of U-937 cell viability upon treatment with 10 μM of various anticancer agents and biological tool molecules. Cell viability was assessed by AV/PI analysis. G) Time course analysis of adherent cell viability upon treatment with Raptinal, 1541B, and Staurosporine (all tested at 10 μM). Cell viability was assessed by AV/PI analysis.

FIG. 2A-H. Raptinal activates the intrinsic pathway and requires functional mitochondria for apoptosis induction. A) Time course immunoblots of mitochondrial and cytosolic fractions of U-937 cells treated with 10 μM Raptinal show cytochrome c release and subsequent caspase-9 activation occur after 20 minutes of treatment. B) Time course immunoblot analysis of caspase-9, -3, and -8 activation in U-937 cells treated with 10 μM Raptinal. C) Relative percent caspase-3/-7 activity of MIA PaCa-2 cells treated with 10 μM Raptinal for 1 hour upon siRNA knockdown of apoptosis genes. D) Jurkat C8−/− are equally susceptible, Jurkat FADD−/− are more susceptible, while Jurkat Bcl-2 overexpressing cells are less susceptible than wild type cells to 10 μM Raptinal as assessed by AV/PI assay after 2 hours. Data represent the mean±SD from 3 independent experiments. **Indicates p values <0.02. E) Transmission electron micrographs of U-937 cells treated with vehicle or 10 μM Raptinal for 5, 30 and 60 minutes. The images show rapid changes in mitochondrial morphology (arrows) after 5 minutes of treatment with Raptinal. At 30 minutes, mitochondria are largely devoid of cristae and at 60 minutes, peripheral nuclear condensation is apparent. Scale bars represent 1 micron. F) Raptinal does not induce cytochrome c release from the mitochondrial pellet into the supernatant of isolated mitochondria treated with Raptinal in vitro under non-respiring conditions. The positive control, pro-apoptotic Bid protein is able to induce cytochrome c release. G) U-937 cells pretreated with various potential cytoprotective agents and inhibitors of various cellular pathways were treated with 10 μM Raptinal for 2 hours and protection from the effects of Raptinal was assessed by AV/PI. Data represent the mean % protection ±SD from 3 independent experiments. *Indicates p values <0.05. H) Protective mitochondrial agents retard cytochrome c release and caspase 9 activation in U-937 cells.

FIG. 3A-F. Raptinal Exhibits Activity in vivo. A) Zebrafish embryos expressing secretory annexin V-YFP exhibit pronounced punctate YFP signal indicating phosphatidylserine externalization following 1.5 hours of treatment with 10 μM Raptinal. B) Quantification of apoptotic cells in Raptinal-versus DMSO-treated zebrafish under the conditions in A. Data represent the mean±SD (n=5 and n=7 embryos for Raptinal and DMSO, respectively; *indicates p value <0.001). Raptinal inhibits subcutaneous B16-F10 melanoma tumor growth in vivo as measured by tumor volume (indicates p value <0.005) in C and tumor mass after tumor excision in D (*indicates p value <0.05). E-F) Raptinal inhibits subcutaneous 4T1 breast cancer tumor growth in vivo as measured by tumor volume (*indicates p value <0.05) in E and tumor mass after tumor excision (*indicates p value <0.05) in F. Arrows in C and E indicate intraperitoneal Raptinal administration at 20 mg/kg once a day. Tumor images in D and F are representative of tumor size at the conclusion of the studies. Data in C, D, E and F represent the mean±SEM (n=7 mice/group). See also FIG. 6A-B.

FIG. 4A-H. Raptinal Induces Rapid Apoptosis in Multiple Cell Lines (cf. FIG. 1). A) Raptinal exists primarily as a hydrate in solution with % conversion of Raptinal dialdehyde to hydrate shown as a function of time (in DMSO/$D_2O$ mixture) by $^1H$ NMR spectroscopy. B) Light microscopy images of U-937 cells treated with 10 μM Raptinal for 30 and 60 min show cellular blebbing that is inhibited by the pan-caspase inhibitor Q-VD-OPh. C) Time course analysis of U-937 cells reveals that Raptinal induces cell death in a time- and concentration dependent manner. Cell viability was assessed by AV/PI. Data represent the mean±SEM from 3 independent experiments. D) Raptinal induces dose-dependent cell death in a variety of cancerous and non-cancerous cell lines at 24 h. E) Immunoblots of SKW 6.4 cells treated with various toxins for 1 hour show prominent activation of caspase-3 by 10 μM Raptinal versus other toxins (all tested at 10 μM). F) Fluorescent caspase-3/-7 activity assay in cell lysate comparing Raptinal to other fast-acting cytotoxins (all tested at 10 μM). G) Immunoblots of adherent HOS, H1993, SK-MEL-5 and MIA PaCa-2 cells show cleavage of PARP-1 and activation of procaspase-3 by 10 μM Raptinal but not other cytotoxins (all tested at 10 μM) after 2 hours. H) Raptinal, unlike 1541B (the procaspase-3 activator), does not directly activate recombinant procaspase-3 in vitro.

FIG. 5A-I. Raptinal Induces Apoptosis Through the Intrinsic Pathway (cf. FIG. 2). A) Time course analysis of cytochrome c in SKW 6.4 cells by Western Blot shows partial cytochrome c release at 10 min and complete release by 20 min of treatment with 10 μM S3 Raptinal. B) Time course analysis of cytochrome c in SKW6.4 (left) and U-937 (right) cells by flow cytometry shows cytochrome c release is partial at 10 minutes and complete release by 20 minutes of treatment with 10 μM of Raptinal. C) Time course immunoblot analysis of caspase-9, -3, and -8 activation in SKW 6.4 cells treated with 10 μM Raptinal. D) Time course immunoblot analysis of caspase-9, -3, and -1 activation and PARP-1 cleavage in U-937 cells treated with 10 μM Raptinal. E) Time course immunoblot analysis of PARP-1 cleavage, caspase-9 activation and MLKL phosphorylation in Raptinal or Q-VD-OPh/CHX/TNF® treated U-937 cells. F) Relative percent caspase-3/-7 activity of MIA PaCa-2 cells treated with 10 μM Raptinal for 1 hour upon siRNA knockdown of APAF1, CASP9 and CASP3 with 3 distinct siRNA constructs. G) U-937 cells exhibit a rapid accumulation of superoxide anion radicals as assessed by dihydroethidium staining and flow cytometry upon 20 minute treatment with Raptinal or thapsigargin but not with etoposide, a topoisomerase II inhibitor. Data represent the mean±SD from 3 independent experiments. H) Raptinal does not induce cytochrome c release from the mitochondrial pellet into the supernatant of isolated mitochondria treated with Raptinal in vitro under respiring conditions. The positive control, pro-apoptotic recombinant Bid protein is able to induce cytochrome c release. I) Raptinal does not induce mitochondrial permeability transition pore (MPTP) in U-937 cells as assessed by a calcein-cobalt quenching assay. Ionomycin in the presence of calcium, a positive control, is able to induce MPTP.

FIG. 6A-B. Bioavailability and Biological Activity of Raptinal in vivo (cf. FIG. 3). A) Pharmacokinetic analysis of Raptinal administered to mice reveals a peak plasma concentration and elimination half-life of 54.4±0.9 μg/ml and 92.1±5.8 minutes, respectively. Data represent the mean±SD from n=3 mice/group. B) Single-dose, intravenous administration of Raptinal across a 4-fold dose range (15-60 mg/kg) does not induce any hematologic toxicity (evaluated 7 days following treatment with Raptinal). Data represent the mean±SD from n=3 mice/group.

DETAILED DESCRIPTION

Figure 2H:
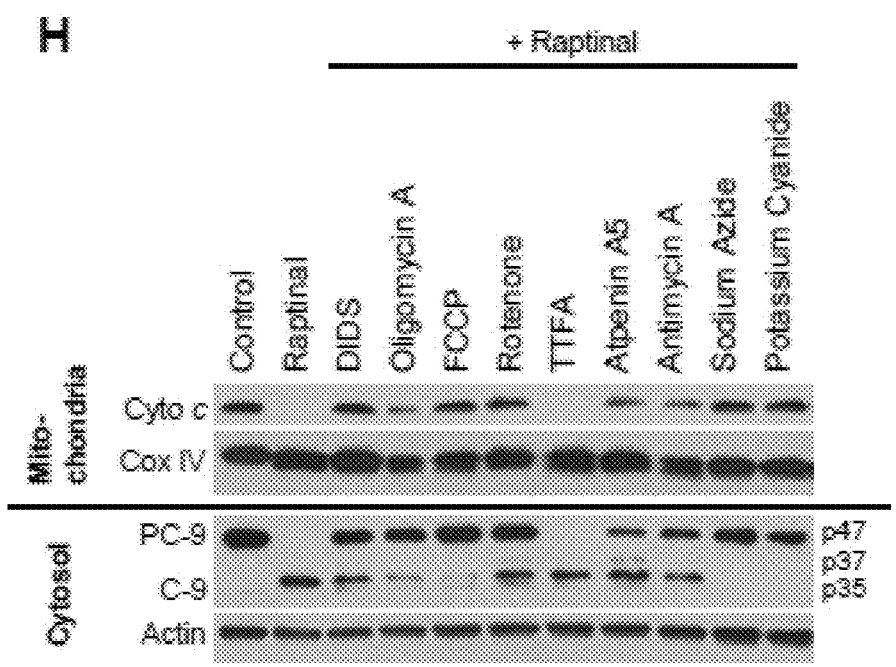

While the present disclosure can take many different forms, for the purpose of promoting an understanding of the principles of the disclosure, reference will now be made to the embodiments illustrated in the drawings and specific language will be used to describe the same. It will nevertheless be understood that no limitation of the scope of the disclosure is thereby intended. Any alterations and further modifications of the described embodiments, and any further applications of the principles of the disclosure as described herein are contemplated as would normally occur to one skilled in the art to which the disclosure relates.

Raptinal (FIG. 1A) was discovered while screening an in-house library of small molecules for cytotoxicity against HL-60 human leukemia cells; as described extensively below Raptinal was found to be an unusually rapid inducer of apoptosis in multiple cell lines. Aside from the skin-irritant properties of Raptinal (Curtin et al., 1965), no other biological activities regarding this small molecule have been previously reported. The compound was resynthesized for these studies and can be easily accessed in two steps on multi-gram scale (see Example 1). NMR spectroscopy experiments show that the hydrate as drawn in FIG. 1A, rather than the dialdehyde form, is the dominant species in aqueous solution (FIG. 4A).

Apoptosis describes a form of programmed cell death characterized by blebbing of the cell membrane leading to the dissociation of apoptotic bodies from the cell body (Balasubramanian et al., 2007; Galluzzi et al., 2012). Consistent with apoptotic morphological changes, U-937 cells treated with 10 μM Raptinal exhibited modest (at 30 min) and extensive (at 60 min) blebbing, as observed by scanning electron and light microscopy (FIGS. 1B and 4B). Another hallmark of apoptosis is externalization of phosphatidylserine on the cell membrane prior to loss of cell membrane integrity, which can be monitored by annexin V/propidium iodide (AV/PI) staining (Galluzzi et al., 2012; Susin et al., 2000). Treatment with 10 μM Raptinal resulted in ~80% loss in U-937 cell viability after just 2 hours of exposure with cells progressing through the AV+/PI− apoptotic quadrant (FIG. 1C). Consistent with caspase-dependent apoptosis, the pan-caspase inhibitor, Q-VD-OPh, quantitatively blocked the loss in cell viability and cellular blebbing (FIGS. 1C and 4B).

Figure 4D:
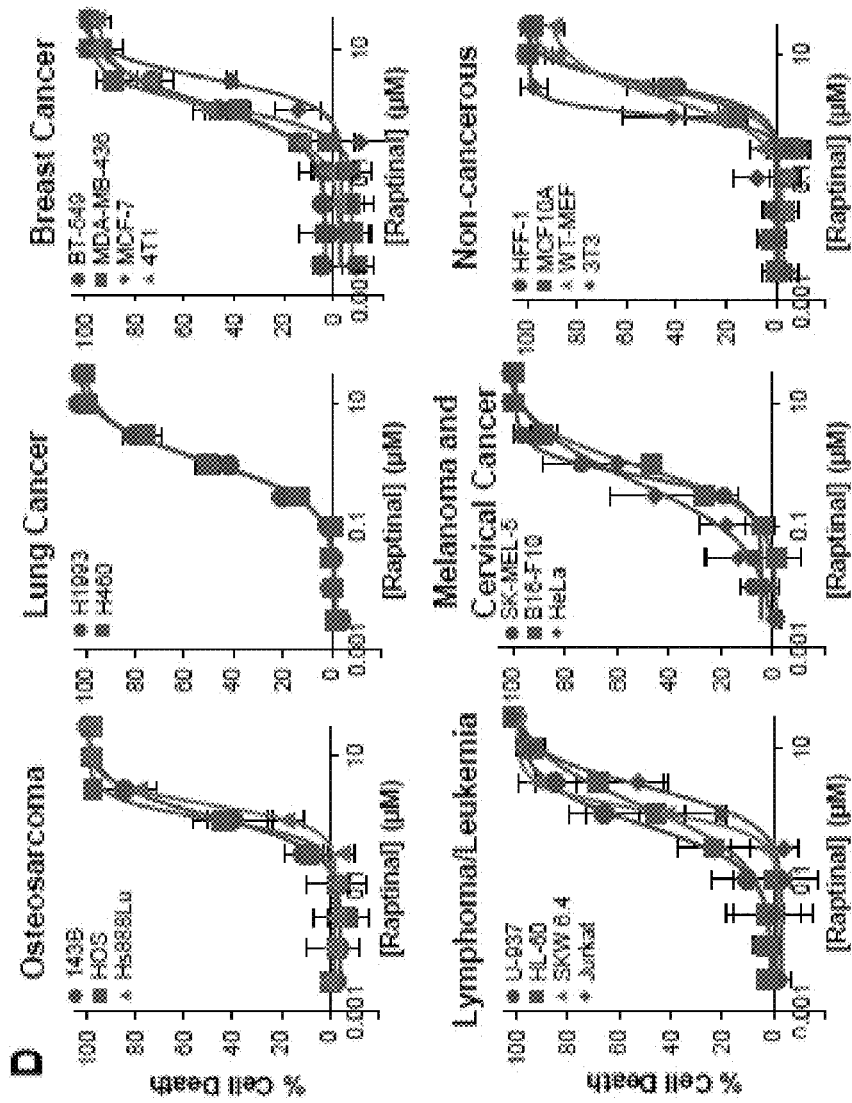

Time course analysis of apoptosis by AV/PI staining with various concentrations of Raptinal revealed the rate of apoptosis was concentration dependent and could be tailored for various applications (FIG. 4C). Additionally, Raptinal was found to induce death against various cancer and non-cancerous cell lines with 24 hour $IC_{50}$ values between 0.7-3.4 μM (Table 1, FIG. 4D), indicating activity across a wide variety of cell lines.

TABLE 1

Raptinal Toxicity in Various Cell Lines. The $IC_{50}$ values of Raptinal against normal and cancer cell lines assessed after 24 hour incubation. Data represent the mean ± SD from 3 independent experiments.

| Cell Line | Cell Type | Average $IC_{50}$ (μM) |
|---|---|---|
| HFF-1 | Human Foreskin Fibroblast | 3.3 ± 0.2 |
| MCF10A | Human Breast Tissue | 3.0 ± 0.2 |
| WT-MEF | Mouse Embryonic Fibroblasts | 2.4 ± 0.7 |
| 3T3 | Mouse Embryonic Fibroblasts | 1.0 ± 0.2 |
| MCF-7 | Human Breast Cancer | 3.4 ± 0.1 |
| BT-549 | Human Breast Cancer | 1.3 ± 0.4 |
| MDA-MB-436 | Human Breast Cancer | 1.1 ± 0.1 |
| 4T1 | Mouse Breast Cancer | 1.0 ± 0.2 |
| SK-MEL-5 | Human Melanoma | 0.7 ± 0.1 |
| B16-F10 | Mouse Melanoma | 1.6 ± 0.2 |
| 143B | Human Osteosarcoma | 1.2 ± 0.5 |
| HOS | Human Osteosarcoma | 1.0 ± 0.1 |
| Hs888Lu | Human Osteosarcoma | 1.7 ± 0.1 |
| SKW 6.4 | Human Lymphoma | 1.1 ± 0.1 |
| U-937 | Human Lymphoma | 0.7 ± 0.3 |
| Jurkat | Human Leukemia | 2.7 ± 0.9 |
| HL-60 | Human Leukemia | 2.1 ± 1.4 |
| HL-60 VCR | Human Leukemia Vincristine Resistant | 1.6 ± 0.5 |
| H460 | Human Lung Cancer | 1.1 ± 0.1 |
| H1993 | Human Lung Cancer | 1.2 ± 0.1 |
| HeLa | Human Cervical Cancer | 0.6 ± 0.4 |
| MIA PaCa-2 | Human Pancreatic Cancer | 1.9 ± 0.8 |

To assess if induction of apoptosis by Raptinal was unusually rapid, 25 other cell death inducing small molecules that encompass a diverse array of mechanisms and biological targets were assessed. Included were inhibitors of kinases (staurosporine and rapamycin), inhibitors of tubulin dynamics (paclitaxel, vincristine, colchicine), topoisomerase inhibitors (camptothecin, etoposide, doxorubicin), DNA alkylators (mitomycin C, cisplatin, MNNG), endoplasmic reticulum/proteasome inhibitors (geldanamycin, thapsigargin, tunicamycin), ROS inducing agents (DNQ (Bair et al., 2010), elesclomol, rotenone, antimycin A) and agents that directly target components of the apoptotic pathway such as Bcl-2 inhibitors (gossypol (Oliver et al., 2005) and HA14-1 (Chen et al., 2002)), XIAP inhibitor (SM-164 (Lu et al., 2008)), apoptosome promoter (AA2 (Nguyen and Wells, 2003)) and direct procaspase-3 activators (PAC-1 (Putt et al., 2006) and 1541/1541B (Wolan et al., 2009)). A concentration of 10 μM was used for all compounds, as most of these molecules are potent inducers of cell death with $IC_{50}$ values typically ranging from the nM to low μM range. Immunoblots after a one hour treatment of U-937 cells showed complete activation of procaspase-3 to caspase-3 by Raptinal, partial activation by 1541, and no activation of procaspase-3 by the other agents (FIG. 1D). Significantly more abundant cleavage of PARP-1 (from 116 to 89 kDa form), a substrate of active caspase-3, was observed in Raptinal treated cells versus the other toxins (FIG. 1D). In SKW 6.4 cells, Raptinal was the only agent capable of inducing procaspase-3 activation after one hour of exposure (FIG. 4E).

AV/PI analyses of U-937 cells after two hours of treatment revealed Raptinal induced 80% loss in cell viability, 1541 reduced viability by 50% (average values, p values <0.05), while the other 24 compounds were unable to affect cell viability (FIG. 1E). Time course AV/PI experiments revealed conventional cytotoxic compounds with similar mechanisms of action shared similar times to 50% cell death (FIG. 1F and Table 2), although no obvious trend was observed for alternative mechanistic apoptotic agents.

TABLE 2

Time to 50% Cell Death for Various Cytotoxins (see also, FIG. 1). The time to 50% cell death in U-937 cells and mechanism of action for the agents tested based on the data in FIG. 1F.

| Molecule | Mechanism | Time to 50% death (hours) |
| --- | --- | --- |
| Raptinal | Intrinsic pathway inducer | 1.5 |
| Staurosporine | Kinase inhibitor | 5 |
| Rapamycin | Kinase inhibitor | >36 |
| Colchicine | Tubulin inhibitor | 15 |
| Vincristine | Tubulin inhibitor | 14 |
| Paclitaxel | Tubulin stabilizer | 18 |
| Camptothecin | Topoisomerase inhibitor | 5 |
| Etoposide | Topoisomerase inhibitor | 5 |
| Doxorubicin | Topoisomerase inhibitor | 6 |
| Mitomycin C | DNA alkylator | 20 |
| Cisplatin | DNA cross-linker | >36 |
| MNNG | DNA alkylator | >36 |
| Thapsigargin | ER/proteasome inhibitor | 14 |
| Tunicamycin | ER/proteasome inhibitor | 24 |
| Geldanamycin | ER/proteasome inhibitor | >36 |
| DNQ | ROS inducer | 6 |
| Elesclomol | ROS inducer | >36 |
| Rotenone | Mitochondrial Complex I inhibitor | 20 |
| Antimycin | A Mitochondrial Complex III inhibitor | >36 |
| Gossypol | Bcl-2 inhibitor | 36 |
| HA-141 | Bcl-2 inhibitor | >36 |
| AA2 | Apoptosome promoter | >36 |
| TPEN | Zinc chelator | 12 |
| PAC-1 | Procaspase-3 activator/Zinc chelator | >36 |
| 1541 | Procaspase-3 activator | 2 |
| SM-164 | XIAP inhibitor | >36 |

The topoisomerase inhibitors required 5-6 hours, whereas agents affecting tubulin polymerization required 14-18 hours (FIG. 1F). Evaluation of Raptinal in a caspase activity assay in cell lysate (utilizing the fluorescent substrate Ac-DEVD-AFC) showed faster induction of caspase-3/-7 activity and higher peak levels when compared to other apoptosis inducing agents, including staurosporine (FIG. 4F). Raptinal, 1541B and staurosporine were evaluated in four adherent cell lines (HOS, H1993, SK-MEL-5, MIA PaCa-2) for their ability to induce cell death as observed by AV/PI staining (FIG. 1G). Raptinal was found to be substantially faster than the other agents and was the only agent capable of activating procaspase-3 and inducing subsequent PARP-1 cleavage within 2 hours of treatment (FIG. 4G). To assess if Raptinal has a direct effect on activation of procaspase-3, recombinant procaspase-3 was treated with up to 100 μM Raptinal; in this experiment (FIG. 4H) no increase in enzymatic activity was observed, in contrast to 1541B, suggesting that Raptinal acts upstream of procaspase-3. A small set of derivatives of Raptinal were synthesized (see Example 1) and assessed to obtain a structure-activity relationship. Evaluation of the ability of these compounds to induce cell death at 2 or 24 hours suggests that the presence of the aldehydes is critical to activity. Unrelated dialdehyde containing molecules were either non-cytotoxic or were slow inducers of death (see FIG. 7).

The Raptinal Mechanism Involves Mitochondrial-Mediated Intrinsic Pathway.

To characterize whether Raptinal-induced apoptosis occurs through the intrinsic or extrinsic pathway, the kinetics of cytochrome c release were determined by fractionating between cytosolic or mitochondrial proteins using selective permeabilization with digitonin combined with analysis by immunoblotting or flow cytometry. Upon treatment of cells with 10 μM Raptinal, cytochrome c release occurs as early as 10 minutes and is nearly complete by 20-30 minutes in both U-937 (FIG. 2A) and SKW 6.4 (FIG. 5A) lymphoma cells by immunoblot and flow cytometry (FIG. 5B). Concomitant with cytochrome c release at 20 minutes is the activation of the initiator caspase-9 (FIGS. 2A and 5A), which proceeds to completion by 45 minutes. Further investigation of caspase activation revealed complete cleavage of not only procaspase-9, but also the initiator procaspase-8 and the executioner procaspase-3 by 45 minutes (FIGS. 2B and 5C).

Co-incubation of cells with the pan-caspase inhibitor Q-VD-OPh and Raptinal resulted in a 19 kDa inhibited form of caspase-3 (which has the pro-domain intact) and completely inhibited the processing of caspase-8 (FIGS. 2B and 5B). This result suggests that the proteolytic cleavage of procaspase-8, a known substrate of caspase-3, occurs downstream of caspase-3, and is consistent with the intrinsic pathway of caspase-dependent apoptosis. To assess the ability of Raptinal to induce apoptosis through other cell death pathways we assessed cells by Western blot for the cleavage of procaspase-1 (pyroptosis/pyronecrosis) and phosphorylation of the RIP3 kinase target MLKL (necroptosis). We saw neither cleavage of procaspase-1 (FIG. 5D) or phosphorylation of MLKL (FIG. 5E). In contrast, phosphorylation of MLKL was observed during the induction of necroptosis by TNFα in the presence of cycloheximide and the pan-caspase inhibitor Q-VD-OPh (FIG. 5E).

In order to further investigate intrinsic pathway-mediated apoptosis, a focused siRNA screen was performed for 55 proteins (single siRNA per target) known to be involved in apoptosis (see Table 5 of U.S. Provisional Patent Application No. 62/242,347 filed Oct. 16, 2015, pages 45-52, which pages are incorporated herein by reference). MIA PaCa-2 cells were used for these screens due to the ease of siRNA transfection. Transfected cells were treated with Raptinal (10 μM for 1 hour) and 19 hit genes were identified that, upon siRNA knockdown, substantially reduced (by >30%) Raptinal-induced caspase-3/7 activity (FIG. 2C). Consistent with an intrinsic pathway mechanism, siRNAs for APAF1, DIABLO, CASP3, BOK, and CASP3 afforded the greatest (75-96%) reduction in caspase-3/7 activity. Three of the most important genes (APAF1, CASP3, CASP9) were followed up using three distinct siRNA constructs for each gene, and the results validated knockdown of these genes efficiently inhibits Raptinal-induced caspase-3/-7 activity (FIG. 5F).

Providing further evidence for apoptosis through the intrinsic pathway, Jurkat cells were utilized that contain either a vector control (WT), caspase-8 deletion, fas-activated death domain (FADD) deletion, or Bcl-2 upregulation. Jurkat caspase-$8^{-/-}$ and FADD$^{-/-}$ cell lines, which are resistant to extrinsic pathway stimuli such as Fas-L and TNF-α (Juo et al., 1998), were equally as sensitive to Raptinal as wild type cells against rapid apoptosis induction (FIG. 2D).

In addition, ectopic expression of anti-apoptotic Bcl-2 conferred partial resistance to Raptinal in short assays (2 hours by AV/PI, p value=0.02, FIG. 2D). These results indicate an involvement of mitochondrial-mediated apoptosis that is independent of caspase-8 and FADD, effectively ruling out the extrinsic pathway. In addition, observations in U-937 cells of morphological changes during Raptinal treatment reveal substantial mitochondrial swelling after 5 minutes with the cristae being clearly visible, in contrast to the untreated cells, as assessed by transmission electron microscopy (FIG. 2E). At 30 and 60 minutes, mitochondria are devoid of cristae and at 60 minutes cells exhibit stage II chromatin condensation (peripheral nuclear condensation) consistent with caspase-activated DNAse (CAD) activity (FIG. 2E) (Susin et al., 2000). Production of reactive oxygen species (ROS) in cells treated with Raptinal for 20 minutes was observed upon incubation with the flow cytometry dye dihydroethidium (DHE) (FIG. 5G), which is sensitive to oxidation by superoxide anion radicals. The insensitivity to caspase-8 deletion, morphological mitochondrial changes, and ROS production all indicate Raptinal acts through the mitochondrial-mediated intrinsic pathway.

Due to the rapid nature of apoptotic induction, Raptinal was investigated for a direct effect on mitochondria. Mitochondria were isolated by differential centrifugation, and cytochrome c release was monitored by Western blot. Raptinal did not directly induce cytochrome c release in isolated mitochondria in vitro under respiring and non-respiring conditions (FIGS. 2F and 5H), whereas Bid, a known pro-apoptotic protein (Gillick and Crompton, 2008), was capable of releasing cytochrome c under both conditions. These results indicate that Raptinal is not able to directly induce cytochrome c release. Furthermore, Raptinal-treated cells did not undergo mitochondrial-permeability-transition-pore (MPTP) formation (FIG. 5I), indicating a mitochondrial outer membrane permeabilization (MOMP) model of cytochrome c release.

Maintenance of Mitochondrial Function is Crucial for Apoptosis.

In order to identify important modulators that are involved in rapid apoptosis, a panel of small molecules that inhibit various processes in the cell were investigated for their effect on Raptinal-induced cell death (FIG. 2G). The panel included the pan-caspase inhibitor Q-VD-OPh as a positive control for protection. Several agents that target the mitochondria were investigated, including inhibitors of respiration, the electron transport chain, and components of the mitochondrial transition pore, such as the voltage-dependent anion channel and cyclophilin D. Also studied were the importance of glycolysis, reactive oxygen species, calcium dependent pathways, granzyme B, transcription, and translation. Cells were pretreated with the putative protective agents for 2 hours at concentrations optimized or previously reported (see Table 3) and subsequently incubated with Raptinal (10 µM) for an additional 2 hours, at which point cell viability was assessed by annexin V/PI in order to identify agents critical to rapid apoptosis induction. Several compounds that affect mitochondrial function were able to afford significant to quantitative protection from Raptinal (FIG. 2G). DIDS, a covalent inhibitor of the voltage-dependent anion channel (VDAC) afforded significant protection from apoptosis (Keinan et al., 2010; Shoshan-Barmatz et al., 2010). A mitochondrial respiration uncoupler (FCCP), electron transport chain inhibitors of complex I (rotenone), complex III (antimycin A), complex IV (sodium azide and potassium cyanide) and the ATP synthase inhibitor (oligomycin A) all provided significant to quantitative protection. Interestingly, complex II inhibition by TTFA or atpenin A5 did not confer significant protection in contrast to complex I, III, and IV inhibition. Other pathways, such as ROS, calcium signaling, transcription, necroptosis, ferroptosis and translation, proved to be less important, since only modest-to-no protection was observed with compounds modulating these processes (FIG. 2G).

TABLE 3

Concentrations of cytoprotective agents and methods for determining working concentrations in cytoprotective assays. See FIG. 2.

| Inhibitor | Concentration | Method |
|---|---|---|
| Q-VD-Oph | 50 µM | Optimized (Liu and Cohen, 2014) |
| DIDS | 2 mM | Optimized (Himi et al., 2002) |
| Oligomycin A | 10 µM | Optimized (Cai et al., 2012 Goldstein et al., 2000) |
| FCCP | 10 µM | Based on literature (Kim et al., 2009) |
| Rotenone | 100 µM | Optimized |
| TTFA | 1 mM | Based on literature (Lemarie et al., 2011 Suzuki et al., 1999) |
| Atpenin A5 | 1 µM | Based on literature (Quinlan et al., 2012) |
| Antimycin A | 100 µM | Optimized |
| Sodium Azide | 1 mM | Optimized (Duewelhenke et al., 2007 Goldstein et al., 2000) |
| Potassium Cyanide | 1 mM | Optimized (Ricci et al., 2003) |
| Cyclosporine A | 10 µM | Based on literature (Eskes et al., 1998) |
| Sodium Fluoride | 1 mM | Based on literature (Nishikimi et al., 2000) |
| Sodium Pyruvate | 5 mM | Based on literature (Yoo et al., 2004) |
| Tempol | 10 mM | Based on literature (Dohare et al., 2014) |
| MnTBAP | 20 µM | Based on literature (Madesh et al., 2009) |
| Dicoumerol | 50 µM | Based on literature (Blanco et al., 2010) |
| Tiron | 10 mM | Based on literature (White et al., 2005) |
| DPI | 10 µM | Based on literature (Manosalva et al., 2015) |
| Allopurinol | 1 mM | Based on literature (Kacimi et al., 2011) |
| N-Acetyl-L-Cysteine | 10 mM | Based on literature (Spagnuolo et al., 2006) |
| Ru360 | 10 µM | Based on literature (Perveen et al., 2014) |
| Ferrostatin-1 | 2 µM | Based on literature (Dixon et al., 2012) |
| Calpain/Cathepsin Inhibitor I | 50 µM | Used at high conc. (Ki-value 0.12-0.23 µM) |

TABLE 3-continued

Concentrations of cytoprotective agents and methods for determining working concentrations in cytoprotective assays. See FIG. 2.

| Inhibitor | Concentration | Method |
|---|---|---|
| Granzyme B Inhibitor I | 50 µM | Used at high conc. (Ki-value 300 nM) |
| Necrostatin-1 | 30 µM | Based on literature (Degterev et al., 2005) |
| Actinomycin D | 2 µM | Based on literature (Jao and Salic, 2008) |
| Cycloheximide | 10 µM | Based on literature (Selvarajah et al., 2013) |

To further study the role of mitochondrial voltage dependent anion function and respiration in protection from cell death, cytochrome c release at 2 hours was evaluated in the presence of mitochondrial inhibitors. Immunoblots of mitochondrial and cytosolic fractions revealed that the small molecules that afforded protection in FIG. 2G were able to delay Raptinal-induced cytochrome c release and subsequent caspase-9 activation (FIG. 2H). These results are consistent with previous suggestions that proton transport may be required for Bax-mediated mitochondrial outer membrane permeabilization (Matsuyama et al., 1998). Utilizing a variety of small molecule modulators in combination with rapid induction of the intrinsic pathway by Raptinal has helped to further validate the importance of voltage dependent anion channel, coupled mitochondrial respiration, electron transport chain function and ATP synthase activity in apoptosis induction.

Raptinal Induces Apoptosis in a Whole Organism and Inhibits Tumor Growth In Vivo.

The unique ability of Raptinal to induce rapid apoptosis may be desirable for investigation of programmed cell death both in cell culture and in vivo. Thus the ability of this compound to elicit rapid apoptosis in a transgenic zebrafish model with a secretory annexin V-YFP as a readout of phosphatidylserine externalization and apoptosis (van Ham et al., 2010) was assessed. Live transgenic zebrafish embryos (24 hours post fertilization) were treated with 10 µM Raptinal for 1.5 hours, and the appearance of the punctate annexin V-YFP signal following Raptinal-treatment was particularly evident in the tail section of the embryos (FIG. 3A). Further analysis revealed 80 cells per fish were apoptotic following Raptinal treatment versus 26 cells per fish for DMSO-treated control (FIG. 3B, p value=0.0002).

To characterize the in vivo pharmacokinetics and tolerability of Raptinal in rodents, C57BL/6 mice were administered intravenous Raptinal across a range of dosages as a one-time injection. When administered intravenously at a dosage of 37.5 mg/kg, the peak plasma concentration and elimination half-life of Raptinal were 54.4±0.9 µg/mL (134.5±2.2 µM) and 92.1±5.8 minutes, respectively (FIG. 6A). Single-dose intravenous Raptinal was well tolerated across a wide dose range (15-60 mg/kg) and did not cause hematologic toxicity as assessed 7 days post-administration (FIG. 6B). To investigate the potential anticancer activities exerted by Raptinal, two syngeneic subcutaneous models of aggressive cancers were then used: B16-F10 melanoma and 4T1 breast cancer. Mice were administered 20 mg/kg of Raptinal via IP injection daily for 3-4 days. In the B16-F10 model, administration of Raptinal during the first three days was sufficient to retard tumor volume and tumor mass by 60% relative to controls (FIGS. 3C and 3D). Similar efficacy was observed for the 4T1 murine breast cancer tumor model with 50% growth inhibition after treatment with Raptinal (FIGS. 3E and 3F). These results indicate that Raptinal exerts anticancer activity in vivo, likely through the induction of apoptosis, and is thus useful for studying rapid induction of apoptosis in in vivo settings. Overall, the activity of Raptinal in zebrafish embryos and aggressive cancer models in mice is promising and points to a conserved cross-species mechanism and the broad applicability of Raptinal's potent and rapid apoptosis induction.

We report the discovery of the compound Raptinal, an unusually rapid inducer of caspase-dependent apoptosis in multiple cell lines and in vivo systems. Raptinal is able to induce apoptosis more rapidly than a diverse panel of 25 other small molecule anticancer agents and biological tool compounds tested at the same concentration (FIGS. 1D, 1E, 1F, 4E, 4F and 4G). Raptinal-induced apoptosis challenges the widely held belief that apoptosis takes a minimum time of several hours (Goldstein et al., 2000). A rapid apoptotic phenotype can have important implications in drug development and treatment regimens as supported by recent studies suggesting the rate and extent of apoptotic induction in cell culture can be used to identify effective regimens and drug combinations for the treatment of cancer patients in the clinic (Bosserman et al., 2012; Strickland et al., 2013).

Time course analyses reveal Raptinal induces cytochrome c release and caspase activation within minutes (FIGS. 2A, 2B, 5A and 5B). Raptinal induces apoptosis strongly in both suspension (FIGS. 1F, 2A, 2B, 5A, 5C) and adherent cell lines (FIGS. 1G, 4G). While we found the time to cell death to be slightly slower in some adherent cell lines (FIG. 1G), Raptinal was still consistently the fastest apoptosis inducing agent in these cell lines. The induction of apoptosis by Raptinal occurs through the intrinsic pathway as supported by the sensitivity of cell lines devoid of functional extrinsic pathway signaling (Jurkat FADD$^{-/-}$ and Casp8$^{-/-}$) and rapid morphological changes in mitochondria (FIGS. 2D and 2E), as well as the extensive protection observed by knockdown of apaf-1 and caspase-9 (FIGS. 2C and 5F).

The delay in time between treatment with most apoptotic agents and initiation of apoptosis allows the influence of secondary events to confound interpretation of experimental results. For example, staurosporine is the current gold-standard compound for rapid apoptotic induction, and as such it has found wide use as a means to induce apoptosis in experiments designed to identify apoptotic regulators (Sakahira et al., 1998; Susin et al., 1999; Yang et al., 1997), in important proteomic profiling experiments (Agard et al., 2012; Dix et al., 2008; Dix et al., 2012; Shimbo et al., 2012), and as an ubiquitous control in cell death and caspase activation experiments. However, as a broad spectrum kinase inhibitor staurosporine initiates multiple events upstream of cytochrome c release, which causes staurosporine-induced apoptotic death to typically take ~6-12 hours (FIG. 1F) and up to >24 h (FIG. 1G), complicating the interpretation of downstream readouts. As shown herein Raptinal-induced apoptosis is markedly faster than staurosporine and induces caspase-3 activity considerably faster than staurosporine in six different cell lines in head-to-head experiments (FIGS. 1D, 1F, 1G, 4E, 4F, 4G). This rapid apoptotic induction limits the involvement of secondary inputs and permits the study of the intrinsic pathway in its latent condition. Consistent with this notion, inhibition of transcription or translation (by pre-treatment with actinomycin D and cycloheximide, respectively) did not prevent or delay Raptinal-induced apoptosis (FIG. 2G). Therefore, as a resource for cell biology, Raptinal will find use as a reagent to rapidly turn on intrinsic-pathway apoptosis while bypassing time-consuming upstream events. Used alone or in combination with other apoptotic modulators, Raptinal should also allow for precise evaluation of cellular caspase processing events. For example, data in FIG. 2B indicate that Raptinal in combination with the appropriate caspase inhibitor would enable evaluating the consequences of rapid caspase-9 activation without the confounding activation of caspase-8 following caspase-3 activation.

Using the rapid phenotype of Raptinal, we demonstrate the essential role of various mitochondrial functions in apoptosis induction. The link between mitochondrial processes and apoptosis has been a challenge to study due to the timing and toxicity issues related to genetic- or small molecule-based perturbations of mitochondrial functions that are otherwise essential in maintaining cell viability. Despite these challenges, studies have linked mitochondrial function to apoptosis. For example, alterations in mitochondrial respiration through genetic mutations have linked electron flux to cytochrome c release (Kwong et al., 2007; Matsuyama et al., 1998). In addition, inhibition of complex III by antimycin A and ATP-synthase activity by oligomycin A have been observed to protect against nitric oxide-induced cytochrome c release and apoptosis (Dairaku et al., 2004). Due to the rapid action of Raptinal, we were able to study this process with a variety of mitochondrial inhibitors and detail the requirement for complex III and ATP-synthase activity for apoptosis induction. We also demonstrate the additional requirement of coupled mitochondrial respiration/membrane potential, complex I and IV function and voltage-dependent anion channel function in engaging apoptosis. Inhibition of these various mitochondrial functions delays cytochrome c release and subsequent caspase activation (FIG. 2H).

Activating apoptosis with rapid modulators at various points along the pathway, either upstream of cytochrome c release with Raptinal, at the point of cytochrome c release with the organotin tributyltin (Nishikimi et al., 2001), or downstream by directly activating procaspase-3 with the combination of 1541B and PAC-1 (Botham et al., 2014), will permit elucidation of the myriad of apoptotic modulators yet to be identified. Raptinal is readily available (gram quantities can be produced in two synthetic steps), in contrast to the light-sensitive and expensive natural product staurosporine (ca $100 for purchase of 1 mg). Convenient access to gram quantities of Raptinal will facilitate experiments that are currently not feasible with staurosporine, such as examination of apoptotic phenotypes in whole organisms at various stages of development. The ability to rapidly induce apoptosis through the mitochondrial pathway using Raptinal will facilitate further study of known apoptotic regulators, and the identification of others; as such, Raptinal should find wide utility in both cell culture and in vivo studies as a superior alternative to staurosporine.

DEFINITIONS

The following definitions are included to provide a clear and consistent understanding of the specification and claims.

As used herein, the recited terms have the following meanings. All other terms and phrases used in this specification have their ordinary meanings as one of skill in the art would understand. Such ordinary meanings may be obtained by reference to technical dictionaries, such as *Howley's Condensed Chemicol Dictionary* 14$^{th}$ Edition, by R. J. Lewis, John Wiley & Sons, New York, N.Y., 2001.

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a compound" includes a plurality of such compounds, so that a compound X includes a plurality of compounds X. It is further noted that the claims may be drafted to exclude any optional element. As such, this statement is intended to serve as antecedent basis for the use of exclusive terminology, such as "solely," "only," and the like, in connection with any element described herein, and/or the recitation of claim elements or use of "negative" limitations.

The term "and/or" means any one of the items, any combination of the items, or all of the items with which this term is associated. The phrases "one or more" and "at least one" are readily understood by one of skill in the art, particularly when read in context of its usage. For example, the phrase can mean one, two, three, four, five, six, ten, 100, or any upper limit approximately 10, 100, or 1000 times higher than a recited lower limit. For example, one or more substituents on a phenyl ring refers to one to five, or one to four, for example if the phenyl ring is disubstituted.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the aspect element. As used herein, "consisting essentially of" does not exclude materials or steps that do not materially affect the basic and novel characteristics of the aspect. In each instance herein any of the terms "comprising", "consisting essentially of" and "consisting of" may be replaced with either of the other two terms. The disclosure illustratively described herein suitably may be practiced in the absence of any element or elements, limitation or limitations which is not specifically disclosed herein.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements. When values are expressed as approximations, by use of the antecedent "about," it will be understood that the particular value without the modifier "about" also forms a further aspect.

The term "about" can refer to a variation of ±5%, ±10%, ±20%, or ±25% of the value specified. For example, "about 50" percent can in some embodiments carry a variation from 45 to 55 percent, or as otherwise defined by a particular claim. For integer ranges, the term "about" can include one or two integers greater than and/or less than a recited integer at each end of the range. Unless indicated otherwise herein, the term "about" is intended to include values, e.g., weight percentages, proximate to the recited range that are equivalent in terms of the functionality of the individual ingredient, composition, or embodiment. The term about can also modify the end-points of a recited range as discussed above in this paragraph.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. It is therefore understood that each unit between two particular units are also disclosed. For example, if 10 to 15 is disclosed, then 11, 12, 13, and 14 are also disclosed, individually, and as part of a range. A recited range (e.g., weight percentages or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents. It will be further understood that the endpoints of each of the ranges are significant both in relation to the other endpoint, and independently of the other endpoint.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, for use in an explicit negative limitation.

Whenever a range is given in the specification, for example, a temperature range, a time range, a carbon chain range, or a composition or concentration range, all intermediate ranges and subranges, as well as all individual values included in the ranges given are intended to be individually included in the disclosure. It will be understood that any subranges or individual values in a range or subrange that are included in the description can be optionally excluded from embodiments of the invention.

The term "contacting" refers to the act of touching, making contact, or of bringing to immediate or close proximity, including at the cellular or molecular level, for example, to bring about a physiological reaction, a chemical reaction, or a physical change, e.g., in a solution, in a reaction mixture, in vitro, or in vivo.

An "effective amount" refers to an amount effective to bring about a recited effect, such as an amount necessary to form products in a reaction mixture. Determination of an effective amount is typically within the capacity of persons skilled in the art. The term "effective amount" is intended to include an amount of a compound or reagent described herein, or an amount of a combination of compounds or reagents described herein, e.g., that is effective to form products in a reaction mixture or to bring about the initiation or inhibition of activity of an enzymatic pathway, or to cause the death of a cell. Thus, an "effective amount" generally means an amount that provides the desired effect.

The terms "inhibit", "inhibiting", and "inhibition" refer to the slowing, halting, or reversing the growth or progression of a disease, infection, condition, or group of cells. The inhibition can be greater than about 20%, 40%, 60%, 80%, 90%, 95%, or 99%, for example, compared to the growth or progression that occurs in the absence of the treatment or contacting.

The terms and expressions which have been employed herein are used as terms of description and not of limitation, and there is no intention in the use of such terms and expressions of excluding any equivalents of the features shown and described or portions thereof, but it is recognized that various modifications are possible within the scope of the disclosure. Thus, it should be understood that although the present disclosure has been specifically disclosed by preferred embodiments, exemplary embodiments and optional features, modification and variation of the concepts herein disclosed may be resorted to by those skilled in the art, and that such modifications and variations are considered to be within the scope of this disclosure as defined by the appended aspects. The specific embodiments provided herein are examples of useful embodiments of the present disclosure and it will be apparent to one skilled in the art that the present disclosure may be carried out using a large number of variations of the devices, device components, methods steps set forth in the present description. As will be apparent to one of skill in the art, methods and devices useful for the present methods can include a varying number of optional composition and processing elements and steps.

When a group of substituents is disclosed herein, it is understood that all individual members of that group and all subgroups, including any isomers, enantiomers, and diastereomers of the group members, are disclosed separately. When a Markush group or other grouping is used herein, all individual members of the group and all combinations and sub-combinations possible of the group are intended to be individually included in the disclosure. When a compound is described herein such that a particular isomer, enantiomer or diastereomer of the compound is not specified, for example, in a formula or in a chemical name, that description is intended to include each isomers and enantiomer of the compound described individual or in any combination. Additionally, unless otherwise specified, all isotopic variants of compounds disclosed herein are intended to be encompassed by the disclosure. For example, it will be understood that any one or more hydrogens in a molecule disclosed can be replaced with deuterium or tritium. Isotopic variants of a molecule are generally useful as standards in assays for the molecule and in chemical and biological research related to the molecule or its use. Methods for making such isotopic variants are known in the art. Specific names of compounds are intended to be exemplary, as it is known that one of ordinary skill in the art can name the same compounds differently.

One of ordinary skill in the art will appreciate that starting materials, biological materials, reagents, synthetic methods, purification methods, analytical methods, assay methods, and biological methods other than those specifically exemplified can be employed in the practice of the disclosure without resort to undue experimentation. All art-known functional equivalents, of any such materials and methods are intended to be included in this disclosure. The terms and expressions which have been employed are used as terms of description and not of limitation, and there is no intention that in the use of such terms and expressions of excluding any equivalents of the features shown and described or portions thereof, but it is recognized that various modifications are possible within the scope of the disclosure. Thus, it should be understood that although the present disclosure has been specifically disclosed by preferred embodiments and optional features, modification and variation of the concepts herein disclosed may be resorted to by those skilled in the art, and that such modifications and variations are considered to be within the scope of this disclosure as defined by the appended aspects.

Compounds of the Invention

In certain embodiments, a compound of the invention can be a compound of Formula I:

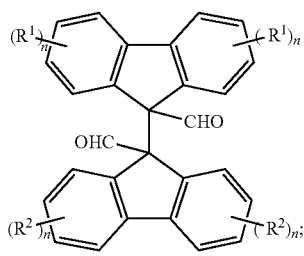

(I)

wherein each $R^1$ and $R^2$ is independently H, halo, nitro, $(C_1$-$C_6)$alkyl, $(C_1$-$C_6)$alkoxy, trifluoromethyl, trifluoromethoxy, —CN, $(C_1$-$C_6)$cycloalkyl, or —N$(R^a)_2$ wherein each $R^a$ is H or $(C_1$-$C_6)$alkyl; and each n is independently 1, 2, 3, or 4; or a salt or solvate thereof.

In various embodiments, a compound of the invention can be a compound of Formula II:

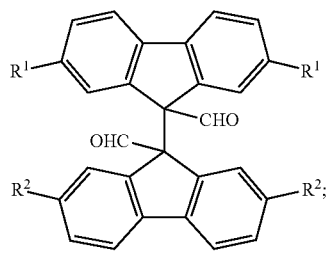

(II)

wherein each $R^1$ and $R^2$ is independently H, halo, nitro, $(C_1$-$C_6)$alkyl, $(C_1$-$C_6)$alkoxy, trifluoromethyl, trifluoromethoxy, —CN, $(C_1$-$C_6)$cycloalkyl, or —N$(R^a)_2$ wherein each $R^a$ is H or $(C_1$-$C_6)$alkyl, or a salt or solvate thereof.

Compounds of Formulas I and II can also be used as their hydrates, e.g., an optionally substituted version of hydrate compound 2 as shown in FIG. 4A. The compounds can be prepared in a manner analogous to the preparation of Raptinal as described in Example 1 below. Various substituted fluorene compounds are available commercially and/or can be prepared according to standard techniques known to those of skill in the art.

In one embodiment, each $R^1$ is halo, such as fluoro, chloro, or bromo. In some embodiments, each $R^2$ is halo, such as fluoro, chloro, or bromo.

In one embodiment, each $R^1$ is nitro. In some embodiments, each $R^2$ is nitro.

In one embodiment, each $R^1$ is $(C_1$-$C_6)$alkyl, such as methyl, ethyl, propyl, or isopropyl. In some embodiments, each $R^2$ is $(C_1$-$C_6)$alkyl, such as methyl, ethyl, propyl, or isopropyl.

In one embodiment, each $R^1$ is $(C_1$-$C_6)$alkoxy, such as methoxy, ethoxy, propoxy, or isopropoxy. In some embodiments, each $R^2$ is $(C_1$-$C_6)$alkoxy, such as methoxy, ethoxy, propoxy, or isopropoxy.

In one embodiment, each $R^1$ is trifluoromethyl. In some embodiments, each $R^2$ is trifluoromethyl.

In one embodiment, each $R^1$ is trifluoromethoxy. In some embodiments, each $R^2$ is trifluoromethoxy.

In one embodiment, each $R^1$ is —CN. In some embodiments, each $R^2$ is —CN.

In one embodiment, each $R^1$ is $(C_1$-$C_6)$cycloalkyl, such as cyclopropyl or cyclohexyl. In some embodiments, each $R^2$ is $(C_1$-$C_6)$cycloalkyl, such as cyclopropyl or cyclohexyl.

In one embodiment, each $R^1$ is —N$(R^a)_2$, such as amino, methylamino, or dimethylamino. In some embodiments, each $R^2$ is —N$(R^a)_2$, such as amino, methylamino, or dimethylamino.

In one specific embodiment, each $R^1$ and $R^2$ is H. In another specific embodiment, each $R^1$ and $R^2$ is Cl. In yet another specific embodiment, each $R^1$ and $R^2$ is bromo.

The invention therefore also relates to methods of making the compounds and compositions of the invention. The compounds and compositions can be prepared by any of the applicable techniques of organic synthesis. Many such techniques are well known in the art. However, many of the known techniques are elaborated in *Compendium of Organic Synthetic Methods* (John Wiley & Sons, New York), Vol. 1, Ian T. Harrison and Shuyen Harrison, 1971; Vol. 2, Ian T. Harrison and Shuyen Harrison, 1974; Vol. 3, Louis S. Hegedus and Leroy Wade, 1977; Vol. 4, Leroy G. Wade, Jr., 1980; Vol. 5, Leroy G. Wade, Jr., 1984; and Vol. 6, Michael B. Smith; as well as standard organic reference texts such as *March's Advanced Organic Chemistry: Reactions, Mechanisms, and Structure*, 5th Ed. by M. B. Smith and J. March (John Wiley & Sons, New York, 2001), *Comprehensive Organic Synthesis; Selectivity, Strategy & Efficiency in Modern Organic Chemistry*, in 9 Volumes, Barry M. Trost, Ed.-in-Chief (Pergamon Press, New York, 1993 printing)); *Advanced Organic Chemistry, Part B: Reactions and Synthesis, Second Edition*, Cary and Sundberg (1983); *Protecting Groups in Organic Synthesis, Second Edition*, Greene, T. W., and Wutz, P. G. M., John Wiley & Sons, New York; and *Comprehensive Organic Transformations*, Larock, R. C., Second Edition, John Wiley & Sons, New York (1999).

A number of exemplary methods for the preparation of the compounds and compositions of the invention are provided herein. These methods are intended to illustrate the nature of such preparations are not intended to limit the scope of applicable methods.

Generally, the reaction conditions such as temperature, reaction time, solvents, work-up procedures, and the like, will be those common in the art for the particular reaction to be performed. The cited reference material, together with material cited therein, contains detailed descriptions of such conditions. Typically, the temperatures will be −100° C. to 200° C., solvents will be aprotic or protic depending on the conditions required, and reaction times will be 1 minute to 10 days. Work-up typically consists of quenching any unreacted reagents followed by partition between a water/organic layer system (extraction) and separation of the layer containing the product.

Oxidation and reduction reactions are typically carried out at temperatures near room temperature (about 20° C.), although for metal hydride reductions frequently the temperature is reduced to 0° C. to −100° C. Heating can also be used when appropriate. Solvents are typically aprotic for reductions and may be either protic or aprotic for oxidations. Reaction times are adjusted to achieve desired conversions.

Condensation reactions are typically carried out at temperatures near room temperature, although for non-equilibrating, kinetically controlled condensations reduced temperatures (0° C. to −100° C.) are also common. Solvents can be either protic (common in equilibrating reactions) or aprotic (common in kinetically controlled reactions). Standard synthetic techniques such as azeotropic removal of reaction by-products and use of anhydrous reaction conditions (e.g. inert gas environments) are common in the art and will be applied when applicable.

Protecting Groups. The term "protecting group", "blocking group", or "PG" refers to any group which, when bound to a hydroxy or other heteroatom prevents undesired reactions from occurring at this group and which can be removed by conventional chemical or enzymatic steps to reestablish the hydroxyl group. The particular removable blocking group employed is not always critical and preferred removable hydroxyl blocking groups include conventional substituents such as, for example, allyl, benzyl, acetyl, chloroacetyl, thiobenzyl, benzylidene, phenacyl, methyl methoxy, silyl ethers (e.g., trimethylsilyl (TMS), t-butyl-diphenylsilyl (TBDPS), or t-butyldimethylsilyl (TBS)) and any other group that can be introduced chemically onto a hydroxyl functionality and later selectively removed either by chemical or enzymatic methods in mild conditions compatible with the nature of the product. The R groups of Formula (I) can also be protecting groups, as described herein.

Suitable hydroxyl protecting groups are known to those skilled in the art and disclosed in more detail in T. W. Greene, *Protecting Groups in Organic Synthesis*; Wiley: New York, 1981 ("Greene") and the references cited therein, and Kocienski, Philip J.; *Protecting Groups* (Georg Thieme Verlag Stuttgart, New York, 1994), both of which are incorporated herein by reference.

Protecting groups are available, commonly known and used, and are optionally used to prevent side reactions with the protected group during synthetic procedures, i.e. routes or methods to prepare the compounds by the methods of the invention. For the most part the decision as to which groups to protect, when to do so, and the nature of the chemical protecting group "PG" will be dependent upon the chemistry of the reaction to be protected against (e.g., acidic, basic, oxidative, reductive or other conditions) and the intended direction of the synthesis.

Protecting groups do not need to be, and generally are not, the same if the compound is substituted with multiple PGs. In general, PG will be used to protect functional groups such as carboxyl, hydroxyl, thio, or amino groups and to thus prevent side reactions or to otherwise facilitate the synthetic efficiency. The order of deprotection to yield free, deprotected groups is dependent upon the intended direction of the synthesis and the reaction conditions to be encountered, and may occur in any order as determined by the artisan.

Various functional groups of the compounds of the invention may be protected. For example, protecting groups for —OH groups (whether hydroxyl, carboxylic acid, or other functions) include "ether- or ester-forming groups". Ether- or ester-forming groups are capable of functioning as chemical protecting groups in the synthetic schemes set forth herein. However, some hydroxyl and thio protecting groups are neither ether-nor ester-forming groups, as will be understood by those skilled in the art. For further detail regarding carboxylic acid protecting groups and other protecting groups for acids, see Greene, cited above. Such groups include by way of example and not limitation, esters, amides, hydrazides, and the like.

Salts and Solvates

Pharmaceutically acceptable salts of compounds described herein are within the scope of the invention and include acid or base addition salts which retain the desired pharmacological activity and are not biologically undesirable (e.g., the salt is not unduly toxic, allergenic, or irritating, and is bioavailable). When a compound has a basic group, such as, for example, an amino group, pharmaceutically acceptable salts can be formed with inorganic acids (such as hydrochloric acid, hydroboric acid, nitric acid, sulfuric acid, and phosphoric acid), organic acids (e.g. alginate, formic acid, acetic acid, benzoic acid, gluconic acid, fumaric acid, oxalic acid, tartaric acid, lactic acid, maleic acid, citric acid, succinic acid, malic acid, methanesulfonic acid, benzenesulfonic acid, naphthalene sulfonic acid, and p-toluenesulfonic acid) or acidic amino acids (such as aspartic acid and glutamic acid). When the compound of the invention has an acidic group, such as for example, a carboxylic acid group, it can form salts with metals, such as alkali and earth alkali metals (e.g. $Na^+$, $Li^+$, $K^+$, $Ca^{2+}$, $Mg^{2+}$, $Zn^{2+}$), ammonia or organic amines (e.g. dicyclohexylamine, trimethylamine, triethylamine, pyridine, picoline, ethanolamine, diethanolamine, triethanolamine) or basic amino acids (e.g. arginine, lysine and ornithine). Such salts can be prepared in situ during isolation and purification of the compounds or by separately reacting the purified compound in its free base or free acid form with a suitable acid or base, respectively, and isolating the salt thus formed.

Many of the molecules disclosed herein contain one or more ionizable groups [groups from which a proton can be removed (e.g., —COOH) or added (e.g., amines) or which can be quaternized (e.g., amines)]. All possible ionic forms of such molecules and salts thereof are intended to be included individually in the disclosure herein. With regard to salts of the compounds described herein, one of ordinary skill in the art can select from among a wide variety of available counterions those that are appropriate for preparation of salts of this invention for a given application. In specific applications, the selection of a given anion or cation for preparation of a salt may result in increased or decreased solubility of that salt.

Examples of suitable salts of the compounds described herein include their hydrochlorides, hydrobromides, sulfates, methanesulfonates, nitrates, maleates, acetates, citrates, fumarates, tartrates (e.g., (+)-tartrates, (−)-tartrates or mixtures thereof including racemic mixtures), succinates, benzoates and salts with amino acids such as glutamic acid. These salts may be prepared by methods known to those skilled in the art. Also included are base addition salts such as sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like. Certain specific compounds of the invention can contain both basic and acidic functionalities that allow the compounds to be converted into either base or acid addition salts.

Certain compounds of the invention can exist in unsolvated forms as well as solvated forms, including hydrated forms. In general, the solvated forms are equivalent to unsolvated forms and are encompassed within the scope of the invention. Certain compounds of the invention may exist in multiple crystalline or amorphous forms. In general, all physical forms are equivalent for the uses contemplated by the invention and are intended to be within the scope of the invention.

The term "solvate" refers to a solid compound that has one or more solvent molecules associated with its solid structure. Solvates can form when a compound is crystallized from a solvent. A solvate forms when one or more solvent molecules become an integral part of the solid crystalline matrix upon solidification. The compounds of the formulas described herein can be solvates, for example, ethanol solvates. Another type of a solvate is a hydrate. A "hydrate" likewise refers to a solid compound that has one or more water molecules intimately associated with its solid or crystalline structure at the molecular level. Hydrates can form when a compound is solidified or crystallized in water, where one or more water molecules become an integral part of the solid crystalline matrix. The compounds of the formulas described herein can be hydrates. As is recognized by those of skill in the art, a dialdehyde can form a hydrate with water by the addition of water, as illustrated in FIG. 4A.

Research Kits

Figure 7:
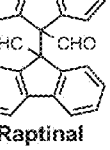
FIG. 7. Activity of Raptinal and derivatives. The $IC_{50}$ values for Raptinal and synthesized derivatives of Raptinal after 24 hour treatment of U-937 cells. Structures are shown in Example 1. Data represent the mean±SD from 3 independent experiments. N.D. indicates not determined.
Figure 7:
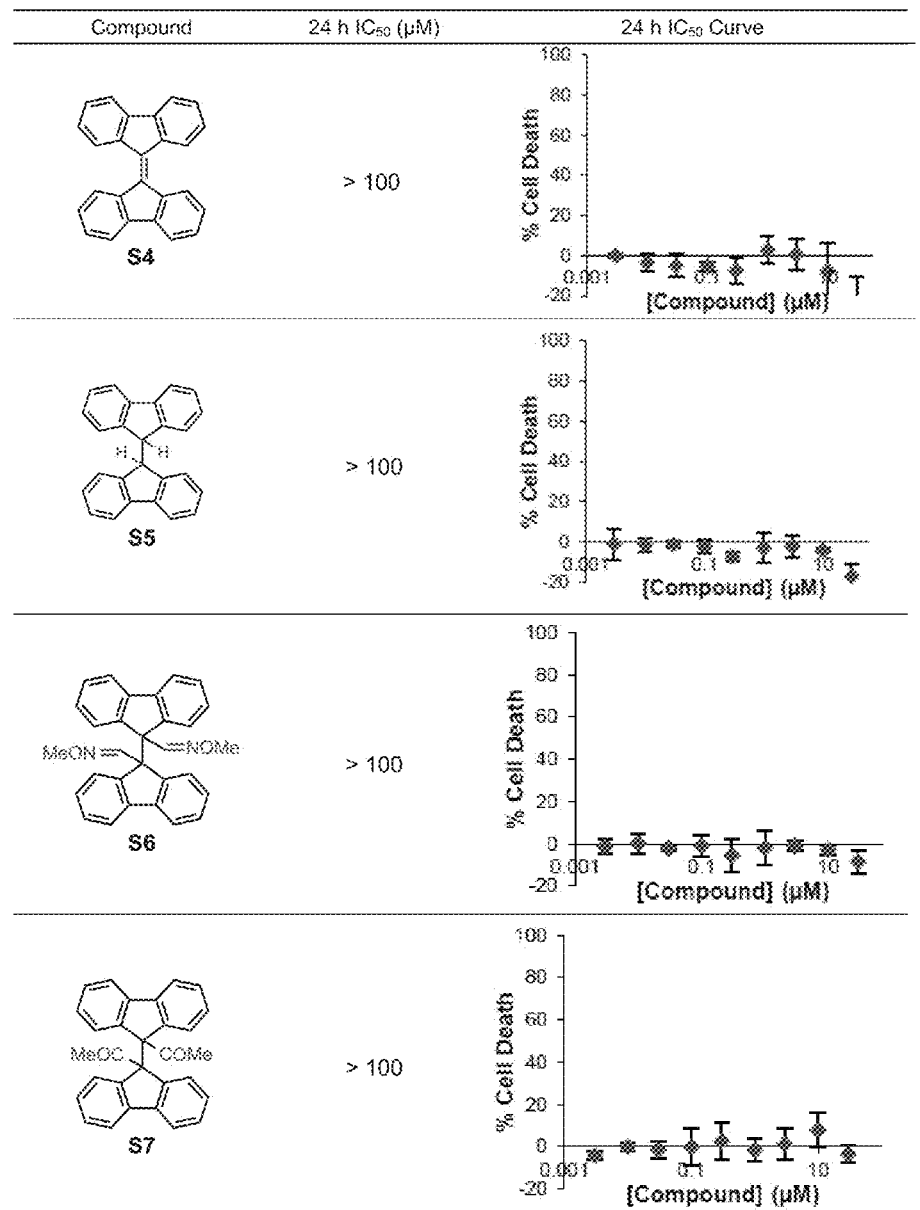
Figure 7:
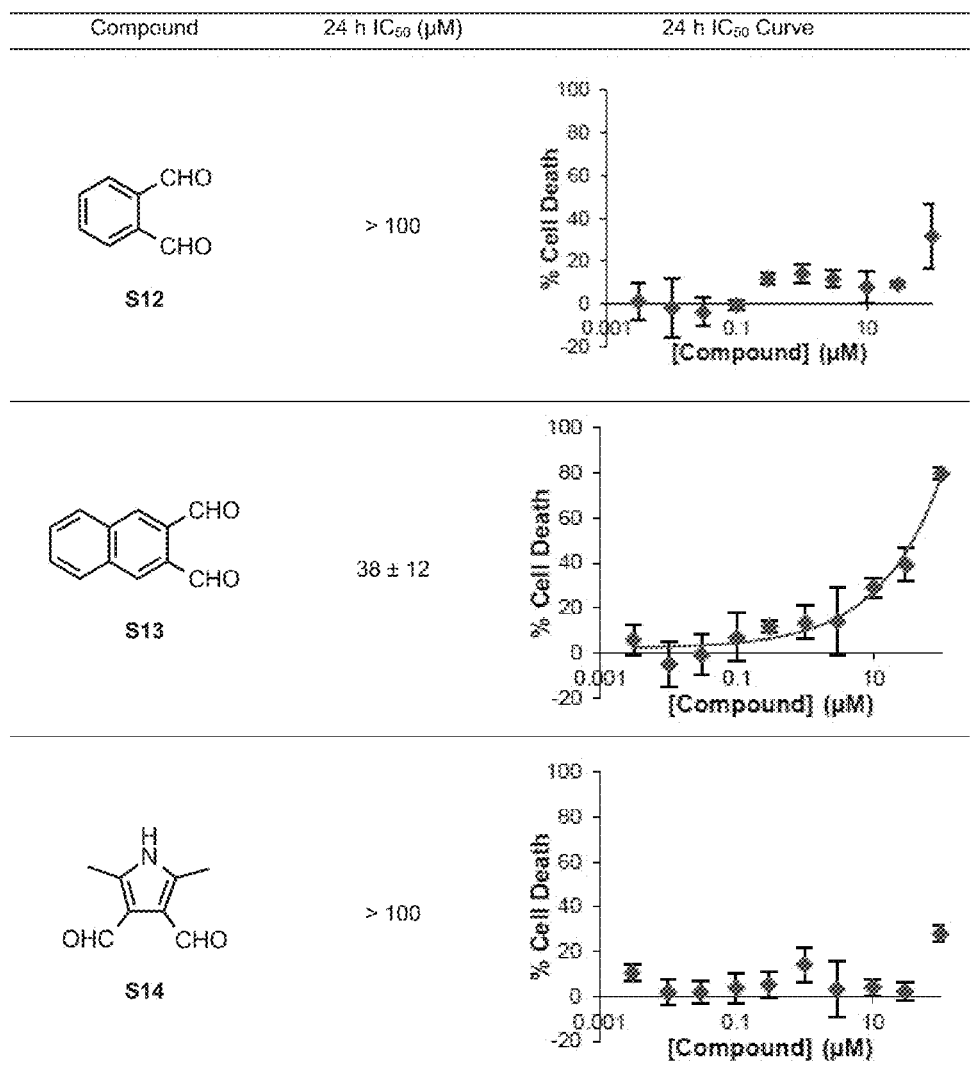

Compounds disclosed herein (e.g., compounds of Formula I, Formula II, or those illustrated in FIG. 7) may be formulated separately in individual compositions wherein each agent is provided as a solid, as a solution, or stably associated with appropriate delivery vehicles. Thus, it is useful to construct kits that include, in separate containers, a first composition comprising delivery vehicles stably associated with at least a first agent and, in a second container, other useful reagents for the use and analysis of the compound and its activity. Containers of salts, buffers, and other reagents may be included. The containers can then be packaged into a kit. The kit can also include instructions as to standard techniques for using the kit, at least including a description of the ratio of amounts of component, e.g., for performing a standard assay. Alternatively, or in addition, the kit is constructed so that the amounts of compositions in each container is pre-measured so that the contents of one container in combination with the contents of the other represent the correct ratio. Alternatively, or in addition, the containers may be marked with a measuring scale permitting dispensation of appropriate amounts according to the scales visible. The containers may themselves be useable in administration or analysis. For example, the kit might contain the appropriate amounts of each composition in separate syringes or vials. Formulations that comprise the pre-formulated correct ratio of agents and reagents may also be packaged in this way so that the formulation is used directly from a syringe or vial prepackaged in the kit.

The disclosure may be further understood by reviewing the following non-limiting Examples. The Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

EXAMPLES

Example 1. Compounds and Compound Preparation

Compounds S4, S5, S12, S13 and S15 are commercially available, were purchased and were used as received. All reactions were run in flame or oven dried glassware under an atmosphere of dry nitrogen unless otherwise noted. Acetonitrile, tetrahydrofuran, methanol and methylene chloride used in reactions were obtained from a solvent dispensing system. Diethyl ether was distilled from sodium metal. 4 Å molecular sieves were dried at 200° C. on high vacuum overnight. Pyridine was distilled from $CaH_2$ and stored on 4 Å molecular sieves. All other reagents were of standard commercial purity and were used as received.

Analytical thin-layer chromatography was performed on EMD Merck silica gel plates with F254 indicator. Plates were visualized with UV light (254 nm) or staining with p-anisaldehyde. Silica gel for column chromatography was purchased from Sorbent Technologies (40-75 μm particle size).

Unless otherwise indicated, $^1H$, $^{13}C$, $^{19}F$, and $^{31}P$ NMR spectra were recorded at 500, 125, 470 and 203 MHz, respectively. $^1H$ and $^{13}C$ NMR spectra were referenced to tetramethylsilane or the residual solvent peak. $^{19}F$ NMR spectra were referenced using $C_6F_6$ as an internal standard (−164.9 ppm). Chemical shifts are reported in ppm and multiplicities are reported as s (singlet), d (doublet), t (triplet), q (quartet), p (pentet), h (hextet), hep (heptet), m (multiplet), and b (broad). Mass spectrometry analysis was performed by the University of Illinois Mass Spectrometry Center.

Procedures for Chemical Synthesis

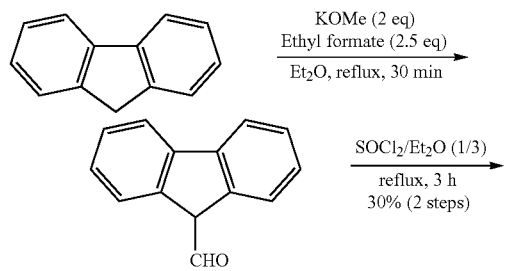

-continued

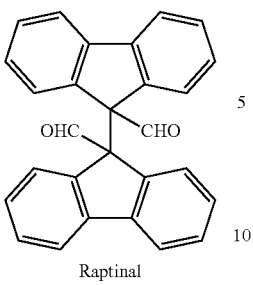

Raptinal

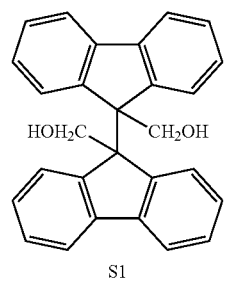

S1

Raptinal:

A modified version of the procedure of Curtin and co-workers was followed (Curtin et al., 1965). To a solution of fluorene (4.4 g, 26.4 mmol, 1 eq) and potassium methoxide (3.7 g, 52.8 mmol, 2 eq) in diethyl ether (50 mL) was added ethyl formate (5.3 mL, 66.0 mmol, 2.5 eq) and the reaction was heated at reflux for 30 min. The reaction was poured into 1M KOH, and the organic layer removed. The aqueous layer was acidified with concentrated HCl until the solution tested acidic to pH paper (at which time a white precipitate was formed). The solution was extracted with diethyl ether, dried through $Na_2SO_4$, and concentrated. The crude material was dissolved in diethyl ether (25 mL), thionyl chloride (8 mL) was added and the solution was heated to reflux for 3 h. The reaction was quenched by careful addition to ice water. The solution was extracted three times with methylene chloride, washed with water and saturated aqueous NaCl, dried through $Na_2SO_4$, and concentrated. The crude material was recrystallized from acetic acid, the crystals were collected and washed with water until the washing solution tested neutral to pH paper, affording Raptinal as white crystals (1.52 g, 30%).

$^1$H NMR (500 MHz, $CDCl_3$) δ 9.89 (s, 2H), 7.53 (dt, J=7.6, 1.0 Hz, 4H), 7.33 (td, J=7.5, 1.1 Hz, 4H), 7.16-7.06 (m, 4H), 6.97 (bd, J=7.8 Hz, 4H). $^{13}$C NMR (125 MHz, $CDCl_3$) δ 197.6, 142.5, 139.6, 129.2, 127.2, 126.8, 119.9, 71.2. HRMS (ESI): m/z 387.1381, [calculated for $C_{28}H_{19}O_2$ (M+H)$^+$: 387.1385].

Raptinal can be isolated as the dialdehyde. Upon contact with water, the dialdehyde enters an equilibrium with its hydrate, as illustrated in FIG. 4A. The dialdehyde form is referred to herein as compound 1, and the hydrate form is referred to as compound 2. See the discussion of FIG. 4A for an equilibrium study of compounds 1 and 2.

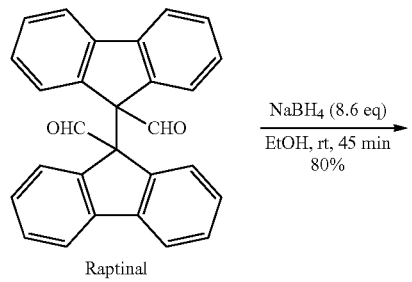

Raptinal

Compound S1:

To a solution of Raptinal (32 mg, 0.0828 mmol, 1 eq) in EtOH (0.8 mL) was added $NaBH_4$ (27 mg, 0.714 mmol, 8.6 eq) and the reaction was stirred for 45 min. The reaction was quenched by careful addition of 1M HCl. The reaction was extracted three times with $CHCl_3$, dried through $Na_2SO_4$, and concentrated. The compound was purified by silica column chromatography to give compound S1 (26 mg, 80%) as a white solid.

$^1$H NMR (500 MHz, $CDCl_3$) δ 7.54 (d, J=7.5 Hz, 4H), 7.27 (t, J=7.5 Hz, 4H), 7.07 (t, J=7.5 Hz, 4H), 6.96 (bs, 4H), 4.10 (s, 4H), 3.45 (bs, 2H). $^{13}$C NMR (125 MHz, $CDCl_3$) δ 145.3, 141.3, 127.9, 126.6, 125.1, 119.7, 67.0, 60.4. HRMS (ESI): m/z 413.1510, [calculated for $C_{28}H_{22}O_2Na$ (M+Na)$^+$: 413.1512].

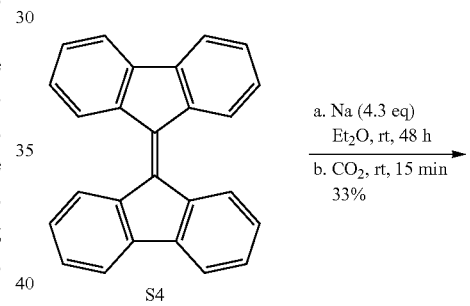

S4

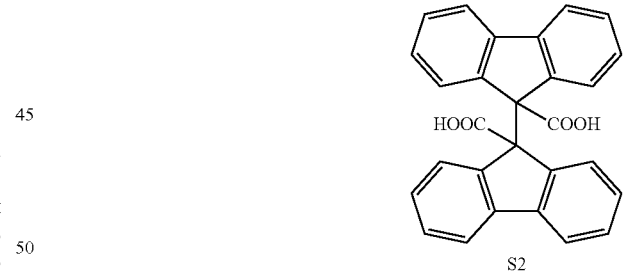

S2

Compound S2:

To a solution of compound S4 (100 mg, 0.304 mmol, 1 eq) in diethyl ether (6 mL) was added sodium metal (30 mg, 1.30 mmol, 4.3 eq). The solution was stirred at room temperature for 48 h, at which point CO2 (g) was bubbled through the solution. The crude reaction was poured into 2.5% NaOH, and washed once with diethyl ether. The aqueous layer was acidified until complete precipitation at which point it was extracted three times with methylene chloride and once with diethyl ether. The organic extracts were combined, dried through $Na_2SO_4$, concentrated and purified by silica column chromatography (with 1% formic acid) to afford compound 52 (42 mg, 33%).

$^1$H NMR (500 MHz, $CD_3OD$) δ 7.42 (d, J=7.5 Hz, 4H), 7.23 (t, J=7.5 Hz, 4H), 7.08 (bs, 4H), 7.00 (t, J=7.5 Hz, 4H).

$^{13}$C NMR (125 MHz, CD$_3$OD) δ 174.7, 143.9, 143.1, 129.2, 128.6, 126.9, 119.8, 67.7. HRMS (ESI): m/z 417.1125, [calculated for C$_{28}$H$_{17}$O$_4$(M−H)$^−$: 417.1127].

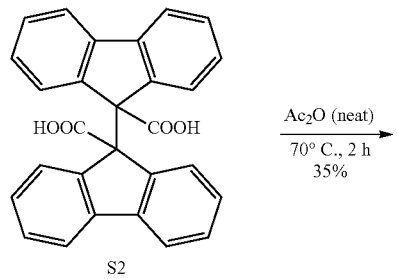

Compound S3:

To a reaction vial was added compound S2 (50 mg, 0.12 mmol, 1 eq) and acetic anhydride (2 mL). The reaction was heated to 70° C. for 2 h, after which the solvent was evaporated. The compound was purified by silica column chromatography to give 16.6 mg (35%) of compound S3.

$^1$H NMR (500 MHz, CDCl$_3$) δ 7.58 (d, J=8 Hz, 4H), 7.39 (bt, J=8 Hz, 4H), 7.20 (bs, 8H). $^{13}$C NMR (125 MHz, CDCl$_3$) δ 169.9, 141.7, 138.4, 130.3, 127.8, 124.7, 120.9, 68.1. HRMS (ESI): m/z 423.1008, [calculated for C$_{28}$H$_{16}$O$_3$Na (M+Na)$^+$: 423.0997].

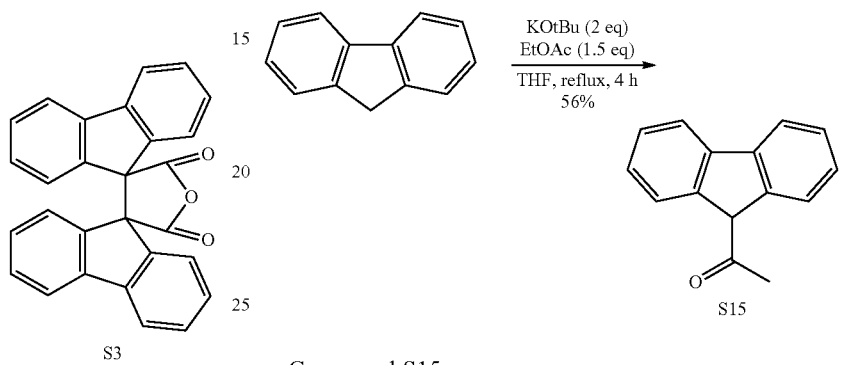

Compound S6:

To a solution of Raptinal (32 mg, 0.083 mmol, 1 eq) in pyridine (0.8 mL) was added methoxyamine hydrochloride (17 mg, 0.207 mmol, 2.5 eq) and the reaction was stirred at room temperature for 44 h. The reaction was diluted with chloroform and washed twice with 1M HCl. The organic layer was dried through Na$_2$SO$_4$, concentrated, and purified by silica column chromatography to afford compound S6 (26 mg, 70%) as a white foam.

$^1$H NMR (500 MHz, CDCl3) δ 8.35 (s, 2H), 7.45 (d, J=7.6 Hz, 4H), 7.25 (t, J=7.7 Hz, 4H), 7.06 (t, J=7.0 Hz, 4H), 6.83 (s, 4H), 3.88 (s, 6H). $^{13}$C NMR (125 MHz, CDCl3) δ 150.1, 143.0, 141.2, 128.2, 126.3, 126.3, 119.4, 62.1, 60.8. HRMS (ESI): 445.1912 [calculated for C$_{30}$H$_{25}$N$_2$O$_2$ (M+H)$^+$ 445.1916].

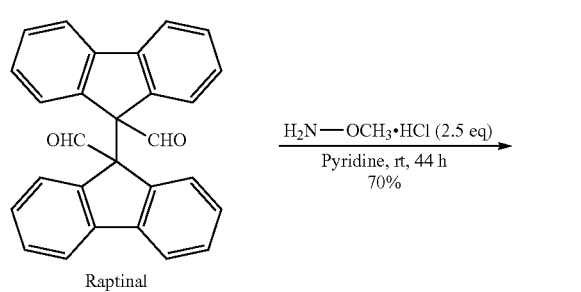

Compound S15:

The procedure of Borowiecki and co-workers was followed and the product matches the known compound (Borowiecki et al., 2013). To a 50 mL round-bottom flask was added fluorene (1.0 g, 6.02 mmol), and potassium t-butoxide (1.01 g, 9.03 mmol, 1.5 eq). The solids were dissolved in THF (20 mL) and ethyl acetate (0.89 ml, 9.03 mmol, 1.5 eq) was added dropwise to the solution. The reaction was heated at reflux under nitrogen for 4 h. The reaction mixture was poured into a saturated solution of NH$_4$Cl and which was extracted three times with diethyl ether. The combined ether extracts were washed with a saturated NaCl solution, dried over Na$_2$SO$_4$, and concentrated in vacuo. The compound was purified by silicia column chromatography to give compound S15 as a yellow solid (699 mg, 56%).

$^1$H NMR (500 MHz, CDCl3) δ 7.82 (d, J=8 Hz, 2H), 7.51 (d, J=7.5 Hz, 2H), 7.46 (t J=7.5 Hz, 2H), 7.35 (t, J=7.5 Hz, 2H), 4.80 (s, 1H), 1.62 (s, 3H). $^{13}$C NMR (125 MHz, CDCl3) δ 207.1, 142.6, 141.6, 128.9, 128.2, 125.6, 120.9, 64.0, 25.6. HRMS (ESI): 209.0970 [calculated mass for C$_{15}$H$_{13}$O (M+H)$^+$ 209.0966].

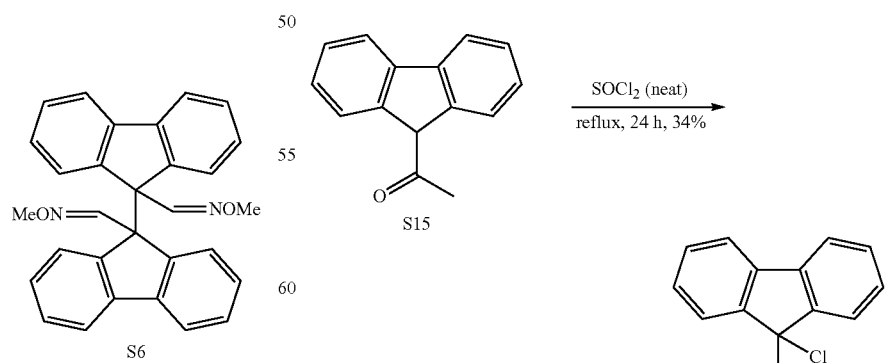

Compound S16:

A modified version of the procedure of Greenhow and co-workers was followed (Greenhow et al., 1954). To a 10 mL round bottom flask containing compound S15 (1.0 g, 4.8 mmol) was added thionyl chloride (4 mL). The reaction was heated at reflux for 24 h. Following removal of thionyl chloride, the product was purified by silica column chromatography (10:1 hexane/ethyl acetate) and recrystallized from ethanol, affording compound S16 (395 mg, 34%).

$^1$H NMR (400 MHz, CDCl$_3$) δ 7.76 (d, J=7.2 Hz, 2H), 7.51 (d, J=7.2 Hz, 2H), 7.49 (td, J=7.6 Hz, 0.8 Hz, 2H), 7.39 (td, J=7.6 Hz, 1.2 Hz, 2H), 1.770 (s, 3H). $^{13}$C NMR (125 MHz, CDCl$_3$) δ 198.8, 144.2, 141.0, 130.8, 129.4, 125.6, 121.3, 110.0, 24.9. HRMS (ESI): 265.0399 [calculated mass for C$_{15}$H$_{11}$OClNa (M+Na)$^+$ 265.0396].

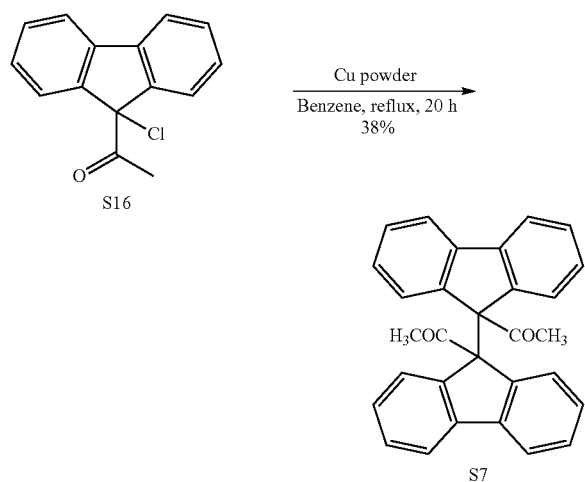

Compound S7:

A modified version of the procedure of Greenhow and co-workers was followed (Greenhow et al., 1954). To a 25 mL round bottom flask containing S16 (169 mg, 0.69 mmol, 1 eq) was added 274 mg of copper powder and 15 mL of benzene. The reaction was heated at reflux for 20 h, the copper was filtered and the solvent was evaporated. The product was purified by silicia column chromatography (10:1 hexane/ethyl acetate) to give compound S7 (55.3 mg, 38%). Note: NMR analysis of the product at room temperature resulted in very poor NMR signal, presumably due to limited rotation about the C9-C9' single bond. NMR spectroscopic analysis was therefore carried out at −40° C.

$^1$H NMR (500 MHz, CDCl$_3$, −40° C.) δ 8.24 (d, J=7.5 Hz, 2H), 7.56 (d, J=7.3 Hz, 2H), 7.53-7.41 (m, 4H), 7.29 (d, J=7.7 Hz, 2H), 7.04 (t, J=7.5 Hz, 2H), 6.63 (t, J=7.5 Hz, 2H), 5.86 (d, J=7.8 Hz, 2H), 1.71 (s, 6H). $^{13}$C NMR (125 MHz, CDCl$_3$, −40° C.) δ 206.4, 144.4, 143.4, 141.3, 141.1, 129.7, 128.9, 128.1, 127.1, 126.1, 125.4, 119.8, 118.9, 72.9, 29.0. HRMS (ESI): 415.1690 [calculated mass for C$_{30}$H$_{23}$O$_2$ (M+H)$^+$ 415.1698].

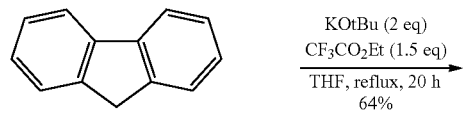

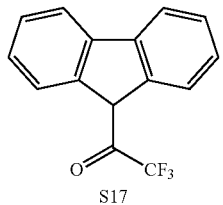

Compound S17:

To an oven-dried 50 mL round-bottom flask with a stir bar was added fluorene (1.0 g, 6.02 mmol) and potassium t-butoxide (1.01 g, 9.03 mmol, 1.5 eq). The solids were dissolved in THF (25 mL) and ethyl trifluoroacetate (1.1 mL, 9.03 mmol, 1.5 eq) was added dropwise. The reaction was heated at reflux under nitrogen for 20 h. The reaction mixture was poured into a saturated NH$_4$Cl solution and extracted three times with diethyl ether. The combined ether extracts were washed with water, dried over Na$_2$SO$_4$, and the solvent was removed in vacuo to give a yellow oil which slowly solidified. The compound was purified by silicia column chromatography (6:1 hexanes/ethyl acetate) to give compound S17 (1.002 g, 64%).

$^1$H NMR (500 MHz, CDCl$_3$) δ 7.83 (d, J=7.5 Hz, 2H), 7.50 (m, 4H), 7.37 (t, J=7 Hz, 2H), 5.25 (s, 1H). $^{13}$C NMR (125 MHz, CDCl$_3$) δ 190.4 (q, J=33.9 Hz), 142.8, 139.1, 129.6, 127.6, 125.7, 121.2, 116.2 (q, J=292.1 Hz), 57.3. $^{19}$F NMR (470 MHz, CDCl$_3$, C$_6$F$_6$) δ: −78.30. HRMS (ESI): m/z 263.0691 [calculated mass for C$_{15}$H$_{10}$OF$_3$ (M+H)$^+$ 263.0684].

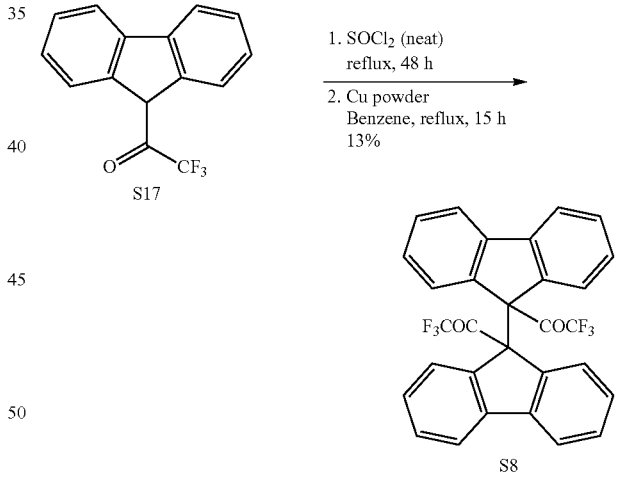

Compound S8:

To a 50 mL round bottom flask containing compound S17 (500 mg, 1.91 mmol) was added thionyl chloride (20 mL). The reaction was heated at reflux for 48 h. The thionyl chloride was removed. 1H NMR showed a compound consistent with the a-chloro trifluoromethyl ketone with partial conversion to the desired dimer. The crude material (426 mg) was added to a 10 mL round bottom flask containing copper powder (827 mg) and benzene (40 mL). The reaction was heated at reflux for 15 h after which the copper was filtered and the solvent evaporated. The product was purified by silica column chromatography (20:1 hexane/ethyl acetate) to give compound S8 (63.4 mg, 13%).

$^1$H NMR (500 MHz, CDCl$_3$) δ 8.23 (bs, 2H), 7.55-7.49 (m, 8H), 7.10 (bs, 2H), 6.66 (bs, 2H), 5.76 (bs, 2H). $^{13}$C NMR (125 MHz, CDCl$_3$) δ 144.5, 142.2, 140.3, 136.6, 130.2, 129.7, 129.4, 127.7, 126.4, 125.6, 120.3, 119.4, 115.7 (q, J=294.5 Hz), 70.0. $^{19}$F NMR (470 MHz, CDCl$_3$, C$_6$F$_6$) δ−74.80. HRMS (ESI) 523.1140 [calculated for C$_{30}$H$_{17}$F$_6$O$_2$ (M+H)$^+$ 523.1133].

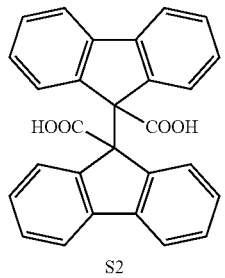

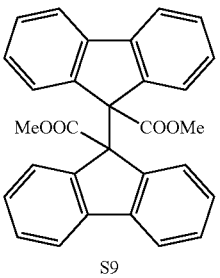

Compound S9:

To a room temperature solution of compound S2 (10 mg, 0.0239 mmol, 1 eq) in methanol (0.3 mL) was added TMS-diazomethane (0.036 mL of a 2M solution in diethyl ether, 0.717 mmol, 3 eq) at room temperature. The reaction was stirred at room temperature for 2 h. The reaction was concentrated and purified by silica column chromatography to afford compound S9 (5.3 mg, 50%) as a white solid.

$^1$H NMR (500 MHz, CDCl$_3$) δ 7.39 (dd, J=7.6, 1.2 Hz, 4H), 7.25 (dd, J=7.8, 6.6 Hz, 4H), 7.08-7.01 (m, 4H), 6.97 (bd, J=7.9 Hz, 4H), 3.77 (s, 6H). $^{13}$C NMR (125 MHz, CDCl$_3$) δ 171.8, 141.7, 141.5, 128.6, 127.4, 126.7, 126.3, 119.0, 66.4, 52.9. HRMS (ESI) 447.1603 [calculated for C$_{30}$H$_{23}$O$_4$(M+H)$^+$ 447.1596].

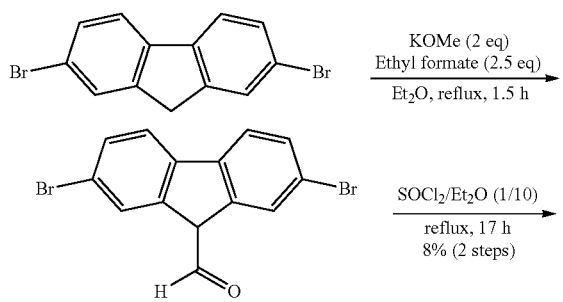

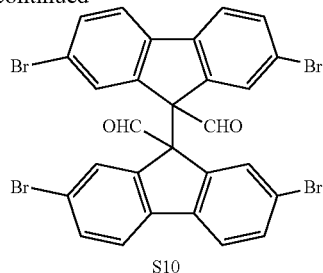

Compound S10:

To a solution of 2,7-dibromofluorene (500 mg, 1.5 mmol, 1 eq) and potassium methoxide (210 mg, 3.0 mmol, 2 eq) in diethyl ether (10 mL) was added ethyl formate (0.3 mL, 3.75 mmol, 2.5 eq) and the reaction was heated to reflux for 1.5 h. The reaction was poured into water and washed with diethyl ether. The aqueous layer was acidified with concentrated HCl until precipitation was observed. The aqueous layer was extracted twice with diethyl ether, washed once with water, dried through Na$_2$SO$_4$ and concentrated. To the crude material was added diethyl ether (10 mL) and thionyl chloride (1 mL) and the reaction was heated at reflux for 17 h. The product was precipitated and washed with diethyl ether to afford compound S10 (42 mg, 8%).

$^1$H NMR (500 MHz, CDCl$_3$) δ 9.80 (s, 2H), 7.49 (d, J=6.6 Hz, 4H), 7.37 (d, J=8.1 Hz, 4H), 7.03 (bs, 4H). $^{13}$C NMR (125 MHz, CDCl$_3$) δ 196.2, 141.0, 140.8, 133.4, 130.6, 121.9, 121.8, 71.5. HRMS (ESI) 724.7595, [calculated for C$_{28}$H$_{14}$O$_2$Br$_4$Na (M+Na)$^+$ 724.7581].

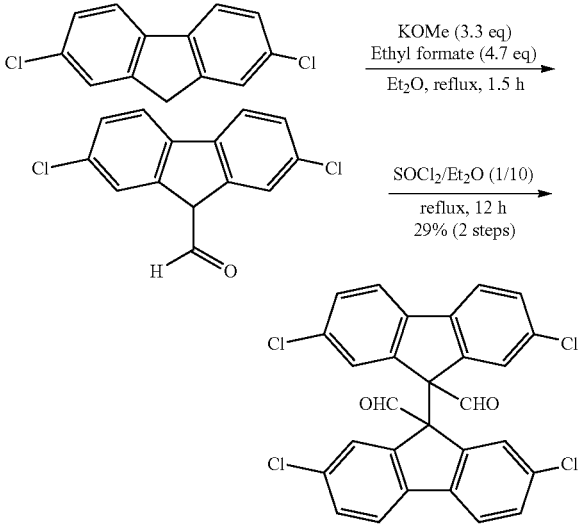

Compound S11:

To a solution of 2,7-dichlorofluorene (1.0 g, 4.25 mmol, 1 eq) and potassium methoxide (1.0 g, 14.2 mmol, 3.3 eq) in diethyl ether (30 mL) was added ethyl formate (1.6 mL, 19.8 mmol, 4.7 eq) and the reaction was heated to reflux for 2.5 h. The reaction was poured into water and extracted twice with hexane. The aqueous layer was acidified with concentrated HCl until precipitation was observed. The aqueous layer was extracted three times with ethyl acetate, the combined organic extracts were washed with saturated aqueous NaCl, dried through Na$_2$SO$_4$ and concentrated. The crude product was dissolved in diethyl ether (5 mL) and thionyl chloride (0.62 mL) was added. The reaction was heated at reflux for 12 h. The precipitate was collected and washed with diethyl ether to give compound S11 (76 mg, 29%).

$^1$H NMR (500 MHz, CDCl$_3$) δ 9.82 (s, 2H), 7.44 (d, J=8.1 Hz, 4H), 7.36 (d, J=8.2 Hz, 4H), 6.91 bs, 4H). $^{13}$C NMR (125 MHz, CDCl$_3$) δ 196.2, 140.9, 140.4, 133.9, 130.5, 127.7, 121.5, 71.3. HRMS (ESI) 522.9849 [calculated for C$_{28}$H$_{15}$O$_2$Cl$_4$ (M+H)$^+$ 522.9826].

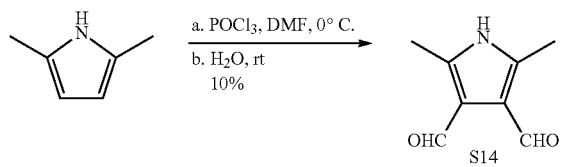

Compound S14:

A modified version of the procedure of Boudif and Momenteau was followed (Boudif and Momenteau, 1996). Briefly, POCl$_3$ (0.33 mL) was added dropwise to DMF (0.5 mL) at 0'C and stirred for 1 h. Next, 2,5-dimethyl-1H-pyrrole (100 mg, 1.05 mmol, 1 eq) was added at room temperature and heated to 50° C. for 2 h. The reaction was cooled to room temperature and slowly quenched by addition to H$_2$O. The reaction was extracted three times with EtOAc and washed with saturated aqueous NaCl. The solution was dried through Na$_2$SO$_4$, concentrated and purified by silica column chromatography to afford compound S14 (16.4 mg, 10%) as a white solid.

$^1$H NMR (500 MHz, d$_6$-Acetone) δ 10.26 (s, 2H), 2.50 (s, 6H). $^{13}$C NMR (125 MHz, d$_3$-Acetone) δ 186.5, 137.9, 120.4, 11.1. HRMS (ESI) 152.0716 [calculated for C$_8$H$_{10}$NO$_2$ (M+H)$^+$ 152.0712].

Example 2. Analysis and Assay Experimental Procedures

Annexin V/PI Cell Viability Analysis

Suspension cells (U-937, SKW 6.4, or Jurkat cell lines) were plated into a 24 well plate (0.5×10$^6$ cells/mL). The drugs of interest were added from DMSO stocks (1% v/v final DMSO). The cells were incubated for the appropriate time after which they were centrifuged and resuspended in annexin V binding buffer containing 1 µg/mL propidium iodide (PI) and 100× dilution of FITC-annexin V (Southern Biotechnology). The samples were analyzed by cell flow cytometry on a Benton Dickinson LSRII flow cytometer. For protection assays, U-937 cells were pretreated with the prospective protective agents for 2 hours at concentrations listed in Example 3, after which the cells were then co-treated with 10 µM Raptinal for 2 hours prior to analysis.

Whole Cell Caspase Activity Assay.

The caspase activity assay was conducted in 96-well plates using transfected cells (see Example 3 for transfection protocol). Transfected cells were treated with 10 µM Raptinal for 1 hour, which corresponded to 40% of maximal caspase-3/-7 activity achievable by Raptinal. After treatment, the media was replaced with PBS (150 µL) and 50 µL of freshly made 4× caspase assay buffer (containing 20 µM Ac-DEVD-AFC) (Stennicke and Salvesen, 1997). After one hour incubation at room temperature (~22° C.) in the dark, the fluorescence of cleaved AFC was read on a spectrofluorometer (Ex: 380 nm, Em: 500 nm). The results were expressed as the relative caspase-3/-7 activity and normalized by designating the vehicle (0.5% DMSO) as 0% activity and Raptinal treatment as 100% activity.

Apoptosis in Zebrofish.

Zebrafish experiments were performed as described (van Ham et al., 2010). TuAB zebrafish embryos were used for all experiments and were incubated at 28° C. in HEPES-buffered E3 zebrafish medium (pH 7.2) in the dark. Chemical treatments (10 µM Raptinal or vehicle, 1% v/v final DMSO) were performed in multi-well plates in buffered E3 medium. Images were taken using an AxioCam MRc camera and AxioVision 4.8 software (Zeiss). To quantify apoptosis, the number of secA5-YFP+ apoptotic cells was counted manually in embryos using a fluorescence dissection stereomicroscope (Discovery V8; Zeiss, Germany).

Syngeneic Tumor Models.

All animal studies were performed with prior approval by the University of Illinois at Urbana-Champaign IACUC committee. B16-F10 cells in HBSS (100 µL of 1×10$^7$ cells/mL) or 4T1 murine breast cancer cells in HBSS (100 µL of 1×10$^7$ cells/mL) were injected subcutaneously into the right flank of shaved and sedated C57BL/6 and BALB/c female mice (6-8 weeks old) for B16-F10 and 4T1 models, respectively. Seven days (for B16-F10) and six days (for 4T1) after inoculation, the mice were randomized based upon tumor size with 7 mice per group. Vehicle or compound was administered intraperitoneally as a corn oil DMSO suspension (300 µL of 10% DMSO in trans fat-free corn oil, 20 mg/kg) once daily for 3 consecutive days for B16-F10 and 4 consecutive days for 4T1 models. Tumor measurements were performed every other day using a caliper and tumor volume was calculated using the equation (0.5×l×w$^2$).

Example 3. Detailed Experimental Procedures

This example provides details for the high throughput toxicity screen assay, immunoblotting procedures, microscopy techniques, reactive-oxygen species assay, cytochrome c release assays, mitochondrial permeability transition pore (MPTP) assay, mitochondrial membrane potential assay, transfection protocol and pharmacokinetic/toxicity profiling.

Reagents for Biological Experiments.

All immunoblotting antibodies (for human PARP-1, caspase-3, caspase-8, caspase-9, caspase-1, cytochrome c, phosphor-MLKL, actin and cox IV) were purchased from Cell Signaling Technologies. Full-length recombinant Bid was purchased from R&D Systems. Human TNFα was purchased from PeproTech. Annexin V-FITC conjugate was obtained from Southern Biotech. Propidium iodide, sulforhodamine B, staurosporine, rapamycin, colchicine, vincristine, paclitaxel, camptothecin, etoposide, doxorubicin, mitomycin C, cisplatin, MNNG, thapsigargin, tunicamycin, rotenone, antimycin A, gossypol, oligomycin A, potassium cyanide, sodium azide, TTFA, HA14-1, TPEN, FCCP, CCCP, DIDS, cyclosporine A, sodium fluoride, tempol, dicoumarol, tiron, diphenyleneiodonium chloride (DPI), allopurinol, N-acetyl-L-cysteine (NAC), calpain inhibitor I, actinomycin D, cycloheximide, dihydroethidium, acridine orange, rhodamine 123 and cobalt (II) chloride were obtained from Sigma Aldrich. Ru360, Q-VD-OPh and granzyme B inhibitor I were obtained from Calbiochem. MnT-BAP hydrochloride were purchased from Santa Cruz Biotechnology. Apoptosis activator 2 (AA2) was purchased from Tocris Biosciences. Atpenin A5 was purchased from Cayman Chemical. Calcein-AM was purchased from Invitrogen. MTS was obtained from Promega Inc. BALB/c and C57Bl/6 female mice (6-8 weeks old) were purchased from Charles River.

Cell Culture Conditions.

All cells were grown in RPMI 1640, DMEM or EMEM media supplemented with 10% FBS, 1% penicillin-streptomycin and incubated at 37° C. in 5% $CO_2$, 95% humidity incubator.

High-Throughput Cell Death Screen.

HL-60 cells were plated into 384 well plates (50 μL of $2\times10^6$ cells/mL per well) in RPMI cell culture media. Library compounds were transferred using a 384-pin transfer apparatus (V & P Scientific, San Diego) which transferred 0.1 μL from 10 mM DMSO stock solutions to achieve a final concentration of 20 μM. Controls containing DMSO only and 10 μM etoposide were used to serve as live and dead controls respectively. The cells were incubated for 24 hours. A solution containing the soluble tetrazolium salt ((3-(4,5-dimethylthiazol-2-yl)-5-(3-carboxymethoxyphenyl)-2-(4-sulfophenyl)-2H-tetrazolium, inner salt; MTS) and the electron coupling reagent, phenazine methosulfate (PMS) was prepared according to the manufacturer's instructions (Promega, Madison Wis.) and 10 μL added to each well. The plates were incubated at 37° C. for approximately an hour after which the formation of the reduced formazan product by viable cells was assessed at 490 nm using a SpectraMax Plus 384 well plate reader (Molecular Devices, Sunnyvale Calif.). The top 220 toxic compounds were selected and retested at 1 μM. Raptinal induced quantitative cell death under these conditions.

MTS Assay for Suspension Cells.

Serial dilutions of compound in 100% DMSO were added in triplicate (2 μL to each well) to empty wells of a 96-well plate. Suspension cells (HL-60, U-937, SKW 6.4, Jurkat W T, Jurkat CASP8$^{-/-}$, Jurkat FADD$^{-/-}$, Jurkat Bcl-2) cells in RPMI 1640 media were added to 96-well plates (198 μL containing $4\times10^4$ cells) and the cells incubated for 24 hours. A solution containing the soluble tetrazolium salt ((3-(4,5-dimethylthiazol-2-yl)-5-(3-carboxymethoxyphenyl)-2-(4-sulfophenyl)-2Htetrazolium, inner salt; MTS) and the electron coupling reagent, phenazine methosulfate (PMS) was prepared according to the manufacturer's instructions (Promega) and 20 μL added to each well. The plates were incubated at 37° C. for 15-45 min and the absorbance at 490 nm was measured using a SpectraMax Plus 384 well plate reader (Molecular Devices, Sunnyvale Calif.). The mean $IC_{50}$ values and standard deviations were determined from three independent experiments.

Sulforhodamine B Assay for Adherent Cells.

Serial dilutions of compound in 100% DMSO were added in triplicate (2 μL to each well) to empty wells of a 96-well plate. Adherent cells (3T3, Hs888Lu, MCF-7, HeLa, WT-MEF, 4T1, B16-F10, SK-MEL-5, MIA PaCa2, BT-549, MDA-MB-436, 143B, HOS, H460, H1993) cells were added to each well ($5\times10^3$ cells in 198 μL of RPMI 1640, DMEM or EMEM media). The plates were incubated for 24 hours. The media was removed from the plate and ice-cold trichloroacetic acid (100 μL of 10% w/v trichloroacetic acid) was added to the plates which were then incubated at 4° C. overnight to fix the cells. The trichloroacetic acid was removed and the wells washed with 200 μL of de-ionized water 5 times. Sulforhodamine B (200 μL of 0.04% sodium salt dissolved in 1% acetic acid) was added to each well and the plates incubated at room temperature for 30 min. Excess sulforhodamine B was removed by washing the plates 5 times with 1% acetic acid. The bound dye was released by the addition of unbuffered Tris-base (200 μL of 10 mM solution) and after a 30 min incubation at room temperature the absorbance at 510 nm was measured (Molecular Devices SpectraMax Plus 384 plate reader). The mean $IC_{50}$ values and standard deviations were determined from three independent experiments.

Immunoblotting.

U-937 cells ($3\times10^6$ cells in 2 mL RPMI) or SKW 6.4 cells ($5\times10^6$ cells in 2 mL RPMI) were treated with compound (1% final DMSO v/v) for the appropriate period of time. After centrifugation and washing with PBS, cells were lysed with RIPA lysis buffer containing protease cocktail inhibitor III (Calbiochem) and cell debris removed by centrifugation (16000×g 5 min). The lysate concentrations were normalized after determination of protein concentration by the Bradford assay and whole cell lysate (40-60 μg) was resolved by 4-20% gradient SDS-PAGE gel electrophoresis at 120 V for 70 min after which proteins were transferred onto PVDF membranes (60 V for 2 hours) and blocked in 5% BSA or fat-free milk in TBST (as per primary antibody manufacturer's instructions) overnight at 4° C. The membranes were blotted for molecules of interest with primary antibody (1:1000 in 5% BSA or milk in TBST) overnight at 4° C. The bound primary antibodies were detected using appropriate secondary HRP conjugated antibodies (1:5000 in TBST) for 1 hour at room temperature and visualized by ECL autoradiography or with an Image Quant LAS 4010. The membranes were stripped in acidic methanol, blocked and re-probed as necessary.

Induction of Necroptosis and Observation of Phospho-MLKL by Immunoblot.

U-937 cells ($1\times10^6$ cells in 1 mL RPMI) were pre-treated with Q-VD-OPh (50 μM) for 30 minutes. Cells were then treated with TNFα (10 ng/ml) in the presence of cycloheximide (20 μg/ml) for (1% final DMSO v/v) for the appropriate period of time. After centrifugation and washing with PBS, cells were lysed with RIPA lysis buffer containing protease cocktail inhibitor III (Calbiochem) and Phosphatase Inhibitor IV (BioVision). Samples were further processed for immunblot analysis as described above.

Cell Morphology by Light Microscopy.

Phase contrast images of U-937 cells treated with 10 μM Raptinal were taken with an Olympus DP-21 microscope digital camera. The cells were kept warm between images by returning the plate to the 37° C. incubator.

Scanning Electron Microscopy.

U-937 cells ($4\times10^6$ cells in 8 mL 0.45 micron-filtered cell culture media) were treated with 1% DMSO) or 10 μM Raptinal in 10 cm culture dishes for 60 minutes. The cells were centrifuged (250×g, 5 min) and the media aspirated. Ice-cold Karnovsky's fixative (1 mL of 0.45 micron filtered) was added to the cell pellet which was resuspended by gently agitation. The cells were fixed overnight at 4° C. and submitted for scanning electron microscopy (SEM) sample processing. The cells were stained with $OsO_4$, placed on filter paper and dehydrated. After mounting, the cells were coated with Pd/Au and scanning electron microscopy was performed.

Transmission Electron Microscopy.

U-937 cells (4 mL of $5\times10^5$ cells/ml) were treated with DMSO or 10 μM of Raptinal for 5, 30, and 60 minutes. The cells were centrifuged 400×g for 5 min and the media aspirated. The cells were fixed by the addition of Karnovsky's fixing solution (0.5 mL) and placed in a 4° C. fridge overnight. The next day, the cells were microwave fixed, stained with 2% $OsO_4$, washed with 3% KCN and enbloc stained with uranyl acetate. The samples were dehydrated with acetonitrile and ethanol, suspended in pure epoxy, and embedded overnight at 85° C. The embedded samples were cut into thick and then thin sections and these were mounted and viewed.

In Vitro Activation of Procaspase-3.

Procaspase-3 was expressed as described previously and purified with Qiagen nickel-NTA resin (Hsu et al., 2012). Increasing concentrations of Raptinal (0, 10, 25, 50 and 100 μM) and 25 μM 1541B were assessed for their capacity to enhance the activity of procaspase-3 over time. 250 nM procaspase-3 was treated with compounds in caspase activity buffer (50 mM HEPES, 50 mM KCl, 0.1 mM EDTA, 10 mM DTT, 0.01% Triton X-100, pH 7.4) and activity was assessed by cleavage of Ac-DEVD-AFC (50 μM) at designated time points.

Protection Assays Using Small Molecule Inhibitors.

For protection assays, U-937 cells ($0.5 \times 10^6$ cells/mL) were pretreated with the prospective protective agents for 2 hours at the following concentrations: Sodium fluoride (1 mM), cyclosporine A (10 μM), oligomycin A (10 μM), FCCP (10 μM), cycloheximide (10 μM), TTFA (1 mM), atpenin A5 (1 μM), actinomycin D (2 μM), rotenone (200 μM), potassium cyanide (1 mM), sodium azide (1 mM) antimycin A (100 μM), sodium pyruvate (5 mM), tempol (10 mM), granzyme B inhibitor 1 (50 μM), calpain inhibitor 1 (50 μM), MnTBAP (20 μM), DPI (10 μM), allopurinol (1 mM), dicoumarol (50 μM), tiron (10 mM), Ru360 (10 μM), ferrostatin-1 (2 μM), necrostatin-1 (30 μM), NAC (10 mM), DIDS (2 mM), and Q-VD-OPh (50 μM). The cells were then co-treated with Raptinal at 10 μM for 2 hours prior to analysis by propidium iodide/FITC-annexin V staining and flow cytometry.

Cytochrome c Release by Immunoblot.

U-937 cells ($3 \times 10^6$ cells in 2 mL RPMI) or SKW 6.4 cells ($5 \times 10^6$ cells in 2 mL RPMI) were treated with 10 μM Raptinal for 10, 20, 30, 45 or 60 minutes in a 12-well plate. Cells were centrifuged (1000×g, 2 min), washed with ice-cold PBS and resuspended in cold 200 μL digitonin permeabilization buffer (75 mM NaCl, 1 mM Sodium phosphate monobasic, 8 mM sodium phosphate dibasic, 250 mM sucrose, 190 μg/mL digitonin, protease cocktail inhibitor, pH 7.5) and placed on ice for 5 min. Cell permeability (>95%) was confirmed by trypan blue. The permeabilized cells were centrifuged (14000×g, 5 min) and 150 μL of supernatant (cytosolic fraction) was saved. The pellet (mitochondrial fraction) was washed in 200 μL digitonin permeabilization buffer and lysed in 25 μL RIPA lysis buffer.

After normalizing samples for protein concentration, 40 μg cytosolic fraction and 50 μg mitochondrial fraction were resolved by electrophoresis on 4-20% SDS-Page gels and immunoblotted for caspase-9 and cytochrome c respectively. Cytosolic immunoblots were re-probed for actin while mitochondrial immunoblots were re-probed with cox IV to confirm equal loading. For protection assays against cytochrome c release, cells were pre-treated with protective agents for 2 hours and co-treated with 10 μM Raptinal for 2 hours. The protective agents were used at the same concentration as listed in the annexin V/propidium iodide assays.

Cytochrome c Release by Flow Cytometry.

Suspension cells ($2.5 \times 10^6$ SKW 6.4 cells or $1.5 \times 10^6$ U-937 cells in 1 mL RPMI) were treated with 10 μM Raptinal in a 24 well plate for 10, 20, 30, 45 and 60 min. The cells were centrifuged (1000×g, 2 min), washed with cold PBS and resuspended in cold permeabilization buffer (PBS containing 50 μg/mL digitonin and 100 mM KCl) and placed on ice for 5 min after which >95% of cells were permeabilized as determined by trypan blue. The cells were fixed by addition of paraformaldehyde (0.5 mL of 8% solution in PBS) by incubating at room temperature for 20 min. The fixed cells were washed three times with 1 mL PBS and blocked in 200 μL blocking buffer (3% BSA, 0.05% saponin in PBS) for 1 hour at room temperature. Anti-cytochrome c monoclonal antibody (Clone 6H2.B4, BD Pharmingen, San Diego, Calif.) was added (200 μL of 1:100 dilution in blocking buffer) to achieve a final antibody dilution of 1:200 and the cells incubated at 4° C. overnight. The cells were pelleted and washed with PBS (1 mL) and secondary antibody added (200 μL of 1:200 dilution of AlexaFluor 488 antimouse antibody in blocking buffer) and the cells incubated at room temperature in the dark. The cells were pelleted and washed with PBS (3 mL) and resuspended in PBS (1 mL) and analyzed by flow cytometry. During acquisition whole intact cells were gated for analysis based on side scatter and forward scatter characteristics.

In Vitro Cytochrome c Release from Isolated Mitochondria.

U-937 cells ($120 \times 10^6$) were washed twice in PBS and resuspended in 800 μL ice-cold lysis buffer (50 mM HEPES, 5 mM DTT, 5 mM PMSF, 25 mM MgCl$_2$, protease cocktail inhibitor, pH 7.5) and the cells were passed through a 26 gauge needle 26 times using a 1 mL syringe until >95% cells were lysed as determined by trypan blue. Isolation buffer (0.25 M sucrose in lysis buffer pH 7.5) was added to the lysed cells (2.4 mL) and mixed by inversion. Debris was removed by centrifugation (500×g. 10 min at 4° C.) and the mitochondria in the supernatant were pelleted by centrifugation (10000×g, 5 min at 4° C.). The mitochondrial pellet was resuspended in washing buffer (2 mL of 50 mM HEPES, 250 mM KCl, 25 mM EDTA, pH 7.5) and incubated on ice for 2 min and centrifuged (12500×g, 5 min). The mitochondrial pellet was resuspended in either non-respiration (300 μL of 50 mM HEPES, 5 mM DTT, 5 mM PMSF, 25 mM MgCl$_2$, protease inhibitor, 250 mM KCl, 25 mM EDTA, pH 7.5) or respiration buffer (300 μL of 50 mM HEPES, 1250 mM sucrose, 5 mM ATP, 0.4 mM ADP, 25 mM sodium succinate, 10 mM potassium phosphate dibasic, pH 7.5). The mitochondria were aliquoted into 18 μL aliquots and Raptinal or recombinant Bid protein added to achieve a final volume of 20 μL The samples were incubated in a 37° C. water bath for 30 min and then the mitochondria were pelleted (16500×g, 5 min at 4° C.). The supernatant was saved (15 μL) and the pellet washed with washing buffer (100 μL), and finally lysed in RIPA lysis buffer (20 μL) and debris removed by centrifugation. Supernatant and pellet lysates were loaded and run on SDS-PAGE gels and processed for immunoblotting of cytochrome c and cox IV (loading control).

Measurement of Cellular ROS Production.

U-937 cells (1 mL of $5 \times 10^5$ cells/mL) in Hank's buffered salt solution (HBSS) containing 5 mM glucose were treated with DMSO, 2 or 10 μM Raptinal, 10 μM thapsigargin, 100 μM etoposide (1% DMSO final) and incubated in the presence of 5 μM dihydroethidium a 37° C., 5% CO$_2$ incubator for 20 minutes. Dihydroethidium is oxidized in the presence of superoxide anion radicals to ethidium, which intercalates DNA and experiences a 24 fold increase in fluorescence. The levels of ethidium were assessed by flow cytometry. Live cells were analyzed based on gating on the forward and side scatter properties and the geometric mean of ethidium staining was determined using the software FCS Express.

Mitochondrial Permeability Transition Pore (MPTP) Calcein-Cobalt Assay.

U-937 cells ($1 \times 10^6$ cells/mL in HBSS) were loaded with calcein-AM (20 nM final concentration) for 45 minutes at 37° C. The cells were washed with HBSS and resuspended in RPMI and plated into a 24-well plate (1×106 cells in 1 mL). The cells were treated with Raptinal (10 µM) for 15, 30, 45, 60 and 90 minutes. Cobalt(II) chloride was added (10 µL of 80 mM stock in HBSS) to the cells 10 minutes prior to the end of the time points. The cells were pelleted and resuspended in HBSS (0.5 mL) and calcein fluorescence was measured by flow cytometry. As a positive control for MPTP, ionomycin and calcium were added to calcein-labeled cells in HBSS 10 minutes prior to analysis by flow cytometry.

Transfection and Screening of siRNA Constructs.

All RNA interference reagents were purchased from Life Technologies (Carlsbad, Calif.). A complete list of siRNAs used can be found in Table 5 of U.S. Provisional Patent Application No. 62/242,347 filed Oct. 16, 2015, pages 45-52, which pages are incorporated herein by reference. The optimal transfection conditions (i.e., siRNA concentration, time, cell number, etc.) were determined using the KDalert GAPDH Assay Kit according to the manufacturer's instructions. Human Silencer Select siRNA was purchased for gene targets of interest and diluted in DEPC water. The siRNA (5 nM final conc.) was complexed in OptiMEM media with RNAiMAX lipofectamine (0.3 µL lipofectamine/pmol siRNA) for 5 min in the well prior to addition of cells. MIA PaCa-2 cells were trypsinized, washed in PBS, resuspended at 50 cells/L in OptiMEM containing 4% FBS, added to the well (100 µL/96-well or 2.5 mL/6-well), and grown for 4 days. Silencer® Negative Control siRNA was used in control wells. After silencing, fresh OptiMEM with 4% FBS was supplied to the cells (half immediately and half at time of compound addition).

Pharmacokinetics and Toxicity Profiling in Mice.

All animal studies were performed with prior approval by the University of Illinois at Urbana-Champaign IACUC committee. Eight week old female C57BL/6 mice were used for all pharmacokinetic and toxicity experiments. For pharmacokinetic profiling, Raptinal was administered at 37.5 mg/kg intravenously and mice were sacrificed in cohorts of 3 at 0, 5, 10, 20, 30, 40, 60, 120, 240, and 360 minutes post-injection, and plasma concentrations of Raptinal were determined by LCMS (n=3 mice/group). For toxicity assessment, Raptinal was administered intravenously as a single-dose injection across a dose range of 15-60 mg/kg, and mice were sacrificed 7 days post-injection for evidence of hematologic toxicity (n=3 mice/group).

Example 3. Pharmaceutical Dosage Forms

The following formulations illustrate representative pharmaceutical dosage forms that may be used for the administration of a compound of a formula described herein (e.g., Raptinal or a derivative thereof), a compound specifically disclosed herein, or a pharmaceutically acceptable salt or solvate thereof (hereinafter referred to as 'Compound X'):

| (i) Tablet 1 | mg/tablet |
|---|---|
| 'Compound X' | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| 'Compound X' | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| 'Compound X' | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/mL) | mg/mL |
|---|---|
| 'Compound X' (free acid form) | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |

| (v) Injection 2 (10 mg/mL) | mg/mL |
|---|---|
| 'Compound X' (free acid form) | 10.0 |
| Monobasic sodium phosphate | 0.3 |
| Dibasic sodium phosphate | 1.1 |
| Polyethylene glycol 400 | 200.0 |
| 0.1N Sodium hydroxide solution (pH adjustment to 7.0-7.5) | q.s. |
| Water for injection | q.s. ad 1 mL |

| (vi) Aerosol | mg/can |
|---|---|
| 'Compound X' | 20 |
| Oleic acid | 10 |
| Trichloromonofluoromethane | 5,000 |
| Dichlorodifluoromethane | 10,000 |
| Dichlorotetrafluoroethane | 5,000 |

| (vii) Topical Gel 1 | wt. % |
|---|---|
| 'Compound X' | 5% |
| Carbomer 934 | 1.25% |
| Triethanolamine (pH adjustment to 5-7) | q.s. |
| Methyl paraben | 0.2% |
| Purified water | q.s. to 100 g |

| (viii) Topical Gel 2 | wt. % |
|---|---|
| 'Compound X' | 5% |
| Methylcellulose | 2% |
| Methyl paraben | 0.2% |
| Propyl paraben | 0.02% |
| Purified water | q.s. to 100 g |

| (ix) Topical Ointment | wt. % |
|---|---|
| 'Compound X' | 5% |
| Propylene glycol | 1% |
| Anhydrous ointment base | 40% |
| Polysorbate 80 | 2% |
| Methyl paraben | 0.2% |
| Purified water | q.s. to 100 g |

| (x) Topical Cream 1 | wt. % |
|---|---|
| 'Compound X' | 5% |
| White bees wax | 10% |
| Liquid paraffin | 30% |

| | |
|---|---|
| Benzyl alcohol | 5% |
| Purified water | q.s. to 100 g |
| (xi) Topical Cream 2 | wt. % |
| 'Compound X' | 5% |
| Stearic acid | 10% |
| Glyceryl monostearate | 3% |
| Polyoxyethylene stearyl ether | 3% |
| Sorbitol | 5% |
| Isopropyl palmitate | 2% |
| Methyl Paraben | 0.2% |
| Purified water | q.s. to 100 g |

These formulations may be prepared by conventional procedures well known in the pharmaceutical art. It will be appreciated that the above pharmaceutical compositions may be varied according to well-known pharmaceutical techniques to accommodate differing amounts and types of active ingredient 'Compound X'. Aerosol formulation (vi) may be used in conjunction with a standard, metered dose aerosol dispenser. Additionally, the specific ingredients and proportions are for illustrative purposes. Ingredients may be exchanged for suitable equivalents and proportions may be varied, according to the desired properties of the dosage form of interest.

CITATIONS

Agard, N. J., Mahrus, S., Trinidad, J. C., Lynn, A., Burlingame, A. L, and Wells, J. A. (2012). Global kinetic analysis of proteolysis via quantitative targeted proteomics. Proc Natl Acad Sci USA 109, 1913-1918.

Bair, J. S., Palchaudhuri, R., and Hergenrother, P. J. (2010). Chemistry and biology of deoxynyboquinone, a potent inducer of cancer cell death. J Am Chem Soc 132, 5469-5478.

Balasubramanian, K., Mirnikjoo, B., and Schroit, A. J. (2007). Regulated externalization of phosphatidylserine at the cell surface: implications for apoptosis. J Biol Chem 282, 18357-18364.

Bosserman, L, Prendergast, F., Herbst, R., Fleisher, M., Salom, E., Strickland, S., Raptis, A., Hallquist, A., Perree, M., Rajurkar, S., et al. (2012). The microculture-kinetic (MiCK) assay: the role of a druginduced apoptosis assay in drug development and clinical care. Cancer Res 72, 3901-3905.

Bossy-Wetzel, E., Newmeyer, D. D., and Green, D. R. (1998). Mitochondrial cytochrome c release in apoptosis occurs upstream of DEVD-specific caspase activation and independently of mitochondrial transmembrane depolarization. Embo J 17, 37-49.

Botham, R. C., Fan, T. M., Im, I., Borst, L. B., Dirikolu, L, and Hergenrother, P J. (2014). Dual smallmolecule targeting of procaspase-3 dramatically enhances zymogen activation and anticancer activity. J Am Chem Soc 136, 1312-1319.

Chen, J., Freeman, A., Liu, J., Dai, Q., and Lee, R. M. (2002). The apoptotic effect of HA14-1, a Bcl-2-interacting small molecular compound, requires Bax translocation and is enhanced by PK11195. Mol Cancer Ther 1, 961-967.

Curtin, D. Y., KampmeieJa, and Farmer, M. L (1965). Nitrosation Reactions of Primary Vinylamines. 3-Amino-2-Phenylindenone. J Am Chem Soc 87, 874-&.

Dairaku, N., Kato, K., Honda, K., Koike, T., Iijima, K., Imatani, A., Sekine, H., Ohara, S., Matsui, H., and Shimosegawa, T. (2004). Oligomycin and antimycin A prevent nitric oxide-induced apoptosis by blocking cytochrome C leakage. J Lab Clin Med 143, 143-151.

Dix, M. M., Simon, G. M., and Cravatt, B. F. (2008). Global mapping of the topography and magnitude of proteolytic events in apoptosis. Cell 134, 679-691.

Dix, M. M., Simon, G. M., Wang, C., Okerberg, E., Patricelli, M. P., and Cravatt, B. F. (2012). Functional interplay between caspase cleavage and phosphorylation sculpts the apoptotic proteome. Cell 150, 426-440.

Dudgeon, C., Qju, W., Sun, Q. H., Zhang, L, and Yu, J. (2009). Transcriptional Regulation of Apoptosis. Essentials of Apoptosis, Second Edition, 239-260.

Ferrer, I. (2006). Apoptosis: future targets for neuroprotective strategies. Cerebrovasc Dis 21 Suppl 2, 9-20.

Fridman, J. S., and Lowe, S. W. (2003). Control of apoptosis by p53. Oncogene 22, 9030-9040.

Fulda, S. (2007). Inhibitor of apoptosis proteins as targets for anticancer therapy. Expert Rev Anticancer Ther 7, 1255-1264.

Galluzzi, L, Vitale, I., Abrams, J. M., Alnemri, E. S., Baehrecke, E. H., Blagosklonny, M. V., Dawson, T. M., Dawson, V. L., El-Deiry, W. S., Fulda, S., et al. (2012). Molecular definitions of cell death subroutines: recommendations of the Nomenclature Committee on Cell Death 2012. Cell Death Differ 19, 107-120.

Gillick, K., and Crompton, M. (2008). Evaluating cytochrome c diffusion in the intermembrane spaces of mitochondria during cytochrome c release. J Cell Sci 121, 618-626.

Goldstein, J. C., Kluck, R. M., and Green, D. R. (2000). A single cell analysis of apoptosis. Ordering the apoptotic phenotype. Ann N Y Acad Sci 926, 132-141.

Goldstein, J. C., Munoz-Pinedo, C., Ricci, J. E., Adams, S. R., Kelekar, A., Schuler, M., Tsien, R. Y., and Green, D. R. (2005). Cytochrome c is released in a single step during apoptosis. Cell Death Differ 12, 453-462.

Hamada, H., Tashima, Y., Kisaka, Y., Iwamoto, K., Hanai, T., Eguchi, Y., and Okamoto, M. (2009). Sophisticated Framework between Cell Cycle Arrest and Apoptosis Induction Based on p53 Dynamics. PLoS ONE 4, e4795.

Juo, P., Kuo, C J., Yuan, J., and Blenis, J. (1998). Essential requirement for caspase-8/FLICE in the initiation of the Fas-induced apoptotic cascade. Current Biology 8, 1001-1008.

Keinan, N., Tyomkin, D., and Shoshan-Barmatz, V. (2010). Oligomerization of the mitochondrial protein voltage-dependent anion channel is coupled to the induction of apoptosis. Mol Cell Biol 30, 5698-5709.

Kwong, J. Q., Henning, M. S., Starkov, A. A., and Manfredi, G. (2007). The mitochondrial respiratory chain is a modulator of apoptosis. J Cell Biol 179, 1163-1177.

Lu, J., Bai, L, Sun, H., Nikolovska-Coleska, Z., McEachern, D., Qju, S., Miller, R. S., Yi, H., Shangary, S., Sun, Y., et al. (2008). SM-164: a novel, bivalent Smac mimetic that induces apoptosis and tumor regression by concurrent removal of the blockade of cIAP-1/2 and XIAP. Cancer Res 68, 9384-9393.

Luetjens, C. M., Kogel, D., Reimertz, C., Dussmann, H., Renz, A., Schulze-Osthoff, K., Nieminen, A. L, Poppe, M., and Prehn, J. H. (2001). Multiple kinetics of mitochondrial cytochrome c release in druginduced apoptosis. Mol Pharm 60, 1008-1019.

Luo, K. Q., Yu, V. C., Pu, Y., and Chang, D. C. (2001). Application of the fluorescence resonance energy transfer method for studying the dynamics of caspase-3 activation during UV-induced apoptosis in living HeLa cells. Biochem Biophys Res Commun 283, 1054-1060.

Matsuyama, S., Xu, Q., Velours, J., and Reed, J. C. (1998). The Mitochondrial F0F1-ATPase proton pump is required for function of the proapoptotic protein Bax in yeast and mammalian cells. Mol Cell 1, 327-336.

Narula, J., Haider, N., Arbustini, E., and Chandrashekhar, Y. (2006). Mechanisms of disease: apoptosis in heart failure—seeing hope in death. Nat Clin Pract Cardiovasc Med 3, 681-688.

Nguyen, J. T., and Wells, J. A. (2003). Direct activation of the apoptosis machinery as a mechanism to target cancer cells. Proc Natl Acad Sci USA 100, 7533-7538.

Nishikimi, A., Kira, Y., Kasahara, E., Sato, E. F., Kanno, T., Utsumi, K., and Inoue, M. (2001). Tributyltin interacts with mitochondria and induces cytochrome c release. Biochem J 356, 621-626.

Oliver, C. L., Miranda, M. B., Shangary, S., Land, S., Wang, S., and Johnson, D. E. (2005). (-)-Gossypol acts directly on the mitochondria to overcome Bcl-2- and Bcl-X(L)-mediated apoptosis resistance. Mol Cancer Ther 4, 23-31.

Putt, K. S., Chen, G. W., Pearson, J. M., Sandhorst, J. S., Hoagland, M. S., Kwon, J. T., Hwang, S. K., Jin, H., Churchwell, M. I., Cho, M. H., et al. (2006). Small-molecule activation of procaspase-3 to caspase-3 as a personalized anticancer strategy. Nat Chem Biol 2, 543-550.

Rehm, M., Dussmann, H., Janicke, R. U., Tavare, J. M., Kogel, D., and Prehn, J. H. M. (2002). Single-cell fluorescence resonance energy transfer analysis demonstrates that caspase activation during apoptosis is a rapid process—Role of caspase-3. J Biol Chem 277, 24506-24514.

Sakahira, H., Enari, M., and Nagata, S. (1998). Cleavage of CAD inhibitor in CAD activation and DNA degradation during apoptosis. Nature 391, 96-99.

Savitski, M. M., Reinhard, F. B., Franken, H., Werner, T., Savitski, M. F., Eberhard, D., Martinez Molina, D., Jafari, R., Dovega, R. B., Klaeger, S., et al. (2014). Tracking cancer drugs in living cells by thermal profiling of the proteome. Science 346, 1255784.

Shimbo, K., Hsu, G. W., Nguyen, H., Mahrus, S., Trinidad, J. C., Burlingame, A. L., and Wells, J. A. (2012). Quantitative profiling of caspase-cleaved substrates reveals different drug-induced and cell-type patterns in apoptosis. Proc Natl Acad Sci USA 109, 12432-12437.

Shoshan-Barmatz, V., Keinan, N., Abu-Hamad, S., Tyomkin, D., and Aram, L (2010). Apoptosis is regulated by the VDAC1 N-terminal region and by VDAC oligomerization: release of cytochrome c, AIF and Smac/Diablo. Biochim Biophys Acta 1797, 1281-1291.

Stennicke, H. R., and Salvesen, G. S. (1997). Biochemical characteristics of caspases-3, -6, -7, and -8. J Biol Chem 272, 25719-25723.

Strickland, S. A., Raptis, A., Hallquist, A., Rutledge, J., Chernick, M., Perree, M., Talbott, M. S., and Presant, C. A. (2013). Correlation of the microculture-kinetic drug-induced apoptosis assay with patient outcomes in initial treatment of adult acute myelocytic leukemia. Leuk Lymphoma 54, 528-534.

Susin, S. A., Daugas, E., Ravagnan, L, Samejima, K., Zamzami, N., Loeffler, M., Costantini, P., Ferri, K. F., Irinopoulou, T., Prevost, M. C., et al. (2000). Two distinct pathways leading to nuclear apoptosis. J Exp Med 192, 571-579.

Susin, S. A., Lorenzo, H. K., Zamzami, N., Marzo, I., Snow, B. E., Brothers, G. M., Mangion, J., Jacotot, E., Costantini, P., Loeffler, M., et al. (1999). Molecular characterization of mitochondrial apoptosisinducing factor. Nature 397, 441-446.

van Ham, T. J., Mapes, J., Kokel, D., and Peterson, R. T. (2010). Live imaging of apoptotic cells in zebrafish. Faseb J 24, 4336-4342.

Wolan, D. W., Zorn, J. A., Gray, D. C., and Wells, J. A. (2009). Small-Molecule Activators of a Proenzyme. Science 326, 853-858.

Wolpaw, A. J., Shimada, K., Skouta, R., Welsch, M. E., Akavia, U. D., Pe'er, D., Shaik, F., Bulinski, J. C., and Stockwell, B. R. (2011). Modulatory profiling identifies mechanisms of small molecule-induced cell death. Proc Natl Acad Sci USA 108, E771-780.

Yang, J., Liu, X., Bhalla, K., Kim, C. N., Ibrado, A. M., Cai, J., Peng, T. I., Jones, D. P., and Wang, X. (1997). Prevention of apoptosis by Bcl-2: release of cytochrome c from mitochondria blocked. Science 275, 1129-1132.

SUPPLEMENTAL CITATIONS

Blanco, E., Bey, E. A., Khemtong, C., Yang, S. G., Setti-Guthi, J., Chen, H., Kessinger, C. W., Carnevale, K. A., Bornmann, W. G., Boothman, D. A., et al. (2010). Beta-lapachone micellar nanotherapeutics for non-small cell lung cancer therapy. Cancer Res 70, 3896-3904.

Borowiecki, P., Baiter, S., Justyniak, I., and Ochal, Z. (2013). First chemoenzymatic synthesis of (R)- and (S)-1-(9H-fluoren-9-yl)ethanol. Tetrahedron-Asymmetry 24, 1120-1126.

Boudif, A., and Momenteau, M. (1996). A new convergent method for porphyrin synthesis based on a '3+1' condensation. Journal of the Chemical Society-Perkin Transactions 1, 1235-1242.

Cai, Q, Zakaria, H. M., Simone, A., and Sheng, Z. H. (2012). Spatial parkin translocation and degradation of damaged mitochondria via mitophagy in live cortical neurons. Curr Biol 22, 545-552.

Curtin, D. Y., KampmeieJa, and Oconnor, B. R. (1965). Nitrosation Reactions of Primary Vinylamines. Possible Divalent Carbon Intermediates. J Am Chem Soc 87, 863-&.

Degterev, A., Huang, Z., Boyce, M., U, Y., Jagtap, P., Mizushima, N., Cuny, G. D., Mitchison, T. J., Moskowitz, M. A., and Yuan, J. (2005). Chemical inhibitor of non-apoptotic cell death with therapeutic potential for ischemic brain injury. Nat Chem Biol 1, 112-119.

Dixon, S. J., Lemberg, K. M., Lamprecht, M. R., Skouta, R., Zaitsev, E. M., Gleason, C. E., Patel, D. N., Bauer, A J., Cantley, A. M., Yang, W. S., et al. (2012). Ferroptosis: an iron-dependent form of nonapoptotic cell death. Cell 149, 1060-1072.

Dohare, P., Hyzinski-Garcia, M. C., Vipani, A., Bowens, N. H., Nalwalk, J. W., Feustel, P. J., Keller, R. W., Jr., Jourd'heuil, D., and Mongin, A. A. (2014). The neuroprotective properties of the superoxide dismutase mimetic tempol correlate with its ability to reduce pathological glutamate release in a rodent model of stroke. Free Radic Biol Med 77, 168-182.

Duewelhenke, N., Krut, O., and Eysel, P. (2007). Influence on mitochondria and cytotoxicity of different antibiotics administered in high concentrations on primary human osteoblasts and cell lines. Antimicrob Agents Chemother 51, 54-63.

Eskes, R., Antonsson, B., Osen-Sand, A., Montessuit, S., Richter, C., Sadoul, R., Mazzei, G., Nichols, A., and Martinou, J. C. (1998). Bax-induced cytochrome C release from mitochondria is independent of the permeability transition pore but highly dependent on Mg2+ ions. J Cell Biol 143, 217-224.

Goldstein, J. C., Waterhouse, N. J., Juin, P., Evan, G. I., and Green, D. R. (2000). The coordinate release of cytochrome c during apoptosis is rapid, complete and kinetically invariant. Nat Cell Biol 2, 156-162.

Greenhow, E. J., Harris, A. S., and White, E. N. (1954). The Chemistry of Fluorene. Part IV. Some New Chloro-Derivatives and Nitro-Derivatives. J Chem Soc, 3116-3121.

Himi, T., Ishizaki, Y., and Murota, S. I. (2002). 4,4'-diisothiocyano-2,2'-stilbenedisulfonate protects cultured cerebellar granule neurons from death. Life Sci 70, 1235-1249.

Hsu, D. C., Roth, H. S., West, D. C., Botham, R. C., Novotny, C J., Schmid, S. C., and Hergenrother, P J. (2012). Parallel Synthesis and Biological Evaluation of 837 Analogues of Procaspase-Activating Compound 1 (PAC-1). ACS Comb Sci 14, 44-50.

Jao, C. Y., and Salic, A. (2008). Exploring RNA transcription and turnover in vivo by using click chemistry. Proc Natl Acad Sci USA 105, 15779-15784.

Kacimi, R., Giffard, R. G., and Yenari, M. A. (2011). Endotoxin-activated microglia injure brain derived endothelial cells via NF-kappaB, JAK-STAT and JNK stress kinase pathways. J Inflamm (Lond) 8, 7.

Kim, T., Wayne Leitner, J., Adochio, R., and Draznin, B. (2009). Knockdown of JNK rescues 3T3-L1 adipocytes from insulin resistance induced by mitochondrial dysfunction. Biochem Biophys Res Commun 378, 772-776.

Lemarie, A., Huc, L, Pazarentzos, E., Mahul-Mellier, A. L., and Grimm, S. (2011). Specific disintegration of complex II succinate:ubiquinone oxidoreductase links pH changes to oxidative stress for apoptosis induction. Cell Death Differ 18, 338-349.

Liu, X., and Cohen, J. I. (2014). Inhibition of Bim enhances replication of varicella-zoster virus and delays plaque formation in virus-infected cells. J Virol 88, 1381-1388.

Madesh, M., Zong, W. X., Hawkins, B. J., Ramasamy, S., Venkatachalam, T., Mukhopadhyay, P., Doonan, P. J., Irrinki, K. M., Rajesh, M., Pacher, P., et al. (2009). Execution of superoxide-induced cell death by the proapoptotic Bcl-2-related proteins Bid and Bak. Mol Cell Biol 29, 3099-3112.

Manosalva, C., Mena, J., Velasquez, Z., Colenso, C. K., Brauchi, S., Burgos, R. A., and Hidalgo, M. A. (2015). Cloning, identification and functional characterization of bovine free fatty acid receptor-1 (FFAR1/GPR40) in neutrophils. PLoS One 10, e0119715.

Nishikimi, A., Uekawa, N., and Yamada, M. (2000). Involvement of glycolytic metabolism in developmental inhibition of rat two-cell embryos by phosphate. J Exp Zool 287, 503-509.

Perveen, S., Yang, J. S., Ha, T J., and Yoon, S. H. (2014). Cyanidin-3-glucoside Inhibits ATP-induced Intracellular Free Ca(2+) Concentration, ROS Formation and Mitochondrial Depolarization in PC12 Cells. Korean J Physiol Pharmacol 18, 297-305.

Quinlan, C. L, Orr, A. L., Perevoshchikova, I. V., Treberg, J. R., Ackrell, B. A., and Brand, M. D. (2012). Mitochondrial complex II can generate reactive oxygen species at high rates in both the forward and reverse reactions. J Biol Chem 287, 27255-27264.

Ricci, J. E., Gottlieb, R. A., and Green, D. R. (2003). Caspase-mediated loss of mitochondrial function and generation of reactive oxygen species during apoptosis. J Cell Biol 160, 65-75.

Selvarajah, J., Nathawat, K., Moumen, A., Ashcroft, M., and Carroll, V. A. (2013). Chemotherapymediated p53-dependent DNA damage response in clear cell renal cell carcinoma: role of the mTORC1/2 and hypoxia-inducible factor pathways. Cell Death Dis 4, e865.

Spagnuolo, G., D'Anto, V., Cosentino, C., Schmalz, G., Schweikl, H., and Rengo, S. (2006). Effect of N-acetyl-L-cysteine on ROS production and cell death caused by HEMA in human primary gingival fibroblasts. Biomaterials 27, 1803-1809.

Suzuki, S., Higuchi, M., Proske, R J., Oridate, N., Hong, W. K., and Lotan, R. (1999). Implication of mitochondria-derived reactive oxygen species, cytochrome C and caspase-3 in N-(4-hydroxyphenyl)retinamide-induced apoptosis in cervical carcinoma cells. Oncogene 18, 6380-6387.

White, R. E., Han, G., Dimitropoulou, C., Zhu, S., Miyake, K., Fulton, D., Dave, S., and Barman, S. A. (2005). Estrogen-induced contraction of coronary arteries is mediated by superoxide generated in vascular smooth muscle. Am J Physiol Heart Circ Physiol 289, H1468-1475.

Yoo, M. H., Lee, J. Y., Lee, S. E., Koh, J. Y., and Yoon, Y. H. (2004). Protection by pyruvate of rat retinal cells against zinc toxicity in vitro, and pressure-induced ischemia in vivo. Invest Ophthalmol Vis Sci 45, 1523-1530.

While specific embodiments have been described above with reference to the disclosed embodiments and examples, such embodiments are only illustrative and do not limit the scope of the invention. Changes and modifications can be made in accordance with ordinary skill in the art without departing from the invention in its broader aspects as defined in the following claims.

All publications, patents, and patent documents are incorporated by reference herein, as though individually incorporated by reference. No limitations inconsistent with this disclosure are to be understood therefrom. The invention has been described with reference to various specific and preferred embodiments and techniques. However, it should be understood that many variations and modifications may be made while remaining within the spirit and scope of the invention.

What is claimed is:

1. A method to induce caspase-dependent apoptosis in an animal cell comprising contacting an animal cell with an effective apoptosis-inducing amount of compound 1 or 2:

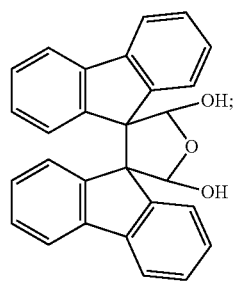

(1)

-continued

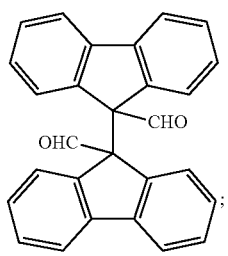
(2)

thereby initiating intrinsic pathway caspase-dependent apoptosis.

2. The method of claim 1 wherein the animal cell is in a live animal.

3. The method of claim 1 wherein the animal cell is in an in vitro cell culture.

4. The method of claim 1 wherein compound 1 or 2 is in a solution or formulation in a concentration of about 0.1 µM to about 20 µM.

5. The method of claim 1 wherein compound 1 or 2 is in a solution or formulation in a concentration of about 1 µM, about 2 µM, about 5 µM, about 10 µM, or about 20 µM.

6. The method of claim 1 wherein the apoptosis occurs within about 6 hours of contacting the cell.

7. The method of claim 1 wherein the apoptosis occurs within about 180 minutes of contacting the cell.

8. A method of inducing initiation of cytochrome c release from the mitochondria of an animal cell comprising contacting an animal cell with an effective cytochrome c releasing amount of compound 1 or compound 2:

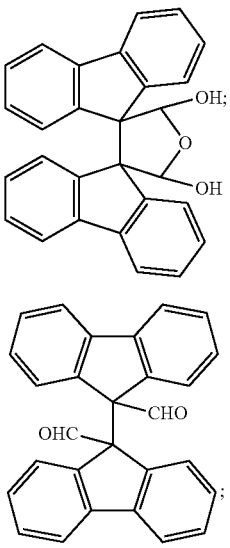

thereby initiating release of cytochrome c from the animal cell.

9. The method of claim 8 wherein the release of cytochrome c from the animal cell is initiated within 60 minutes of contacting the cell.

10. The method of claim 8 wherein the release of cytochrome c from the animal cell is initiated within 30 minutes of contacting the cell.

11. The method of claim 8 further comprising pretreating the cell with a cytoprotective agent or an inhibitor of a cellular pathway, and assessing cytochrome c release from the cell.

12. The method of claim 11 wherein the cytoprotective agent or inhibitor is a mitochondrial inhibitor, an inhibitor of respiration or the electron transport chain, a component of the mitochondrial transition pore, or an inhibitor of glycolysis, reactive oxygen species, calcium dependent pathways, granzyme B, transcription, or translation.

13. The method of claim 11 wherein the pretreating is carried out for about 1-3 hours.

14. The method of claim 10 further comprising contacting the cells with compound 1 or 2 in combination with the pan-caspase inhibitor Q-VD-OPh.

15. The method of claim 11 further comprising analyzing components of the cell for additional apoptotic regulators.

16. The method of claim 8 wherein the cell is contacted with compound 1 or compound 2 in combination with a caspase inhibitor, and the consequences of rapid caspase-9 activation without activation of caspase-8 following caspase-3 activation are evaluated.

17. A method of killing or inhibiting the growth of a cancer cell comprising contacting a cancer cell with an effective anticancer amount of compound 1 or 2:

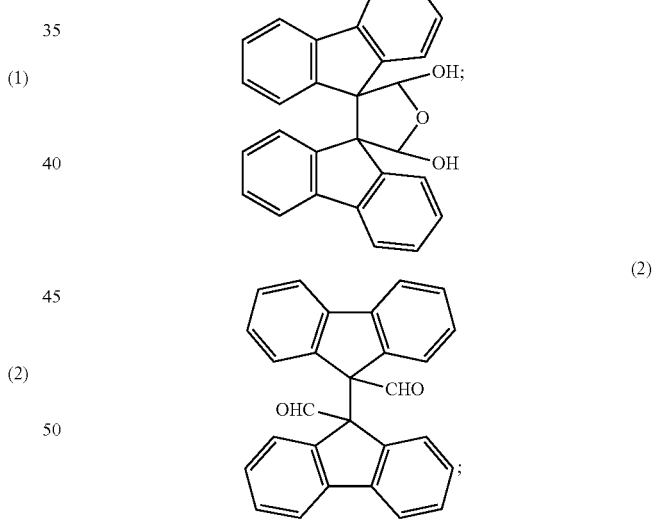

thereby killing or inhibiting the growth of the cancer cell.

18. The method of claim 17 wherein the cancer cell is a breast cancer cell, a cervical cancer cell, a leukemia cell, a lymphoma cell, a lung cancer cell, a melanoma cell, or an osteosarcoma cell.

19. A method of inducing caspase-3/-7 activity and inducing subsequent PARP-1 cleavage in a cell within 2 hours comprising contacting an animal cell with an effective amount of compound 1 or compound 2:

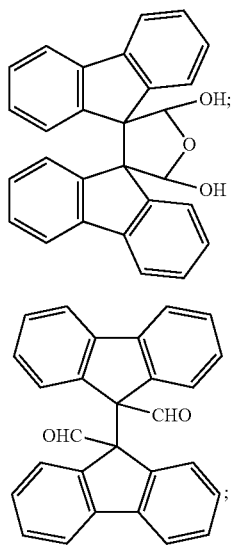
(1)
(2)
thereby inducing caspase-3/-7 activity and inducing subsequent PARP-1 cleavage in the cell.
20. A composition comprising compound 1:
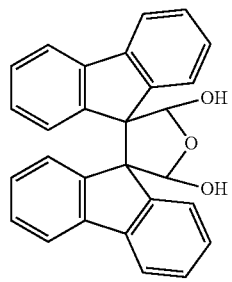
(1)
and water.